US011203583B2

(12) United States Patent
Chevalier et al.

(10) Patent No.: US 11,203,583 B2
(45) Date of Patent: *Dec. 21, 2021

(54) PRODRUG AND PROFLUORESCENT COMPOUNDS FOR SELECTIVE MITOCHONDRIAL IMAGING AND THERAPEUTIC TARGETING

(71) Applicant: ARIZONA BOARD OF REGENTS ON BEHALF OF ARIZONA STATE UNIVERSITY, Scottsdale, AZ (US)

(72) Inventors: Arnaud Chevalier, La ville-du-Bois (FR); Omar Khdour, Phoenix, AZ (US); Yanmin Zhang, Tempe, AZ (US); Sidney Hecht, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/784,202

(22) Filed: Feb. 6, 2020

(65) Prior Publication Data

US 2020/0247775 A1 Aug. 6, 2020

Related U.S. Application Data

(63) Continuation of application No. 16/310,305, filed as application No. PCT/US2017/037253 on Jun. 13, 2017, now Pat. No. 10,604,501.

(60) Provisional application No. 62/350,557, filed on Jun. 15, 2016.

(51) Int. Cl.
| | | |
|---|---|---|
| C07D 321/00 | (2006.01) | |
| C07D 311/06 | (2006.01) | |
| C07D 311/58 | (2006.01) | |
| C07D 403/08 | (2006.01) | |
| C07D 405/04 | (2006.01) | |
| C07D 413/04 | (2006.01) | |
| C07D 417/04 | (2006.01) | |
| C07D 487/14 | (2006.01) | |
| C07D 493/10 | (2006.01) | |
| A61K 47/54 | (2017.01) | |
| A61K 49/00 | (2006.01) | |
| G01N 33/58 | (2006.01) | |

(52) U.S. Cl.
CPC .......... *C07D 321/00* (2013.01); *C07D 311/06* (2013.01); *C07D 311/58* (2013.01); *C07D 403/08* (2013.01); *C07D 405/04* (2013.01); *C07D 413/04* (2013.01); *C07D 417/04* (2013.01); *C07D 487/14* (2013.01); *C07D 493/10* (2013.01); *A61K 47/545* (2017.08); *A61K 49/0052* (2013.01); *G01N 33/582* (2013.01)

(58) Field of Classification Search
CPC .. C07D 321/00; C07D 493/10; C07D 487/14; C07D 417/04; C07D 413/04; C07D 405/04; C07D 403/08; C07D 311/58; C07D 311/06; C07D 311/72; C07D 209/12; C07D 493/14; C07D 491/22; G01N 33/582; G01N 33/533; A61K 49/0052; A61K 47/545; A61K 49/0032; A61K 47/50; C07K 5/1019; C07K 5/00; C07J 41/0044; C07H 15/26
See application file for complete search history.

(56) References Cited

U.S. PATENT DOCUMENTS

| 8,952,025 | B2 | 2/2015 | Hecht |
| 9,102,626 | B2 | 8/2015 | Hecht |
| 9,334,250 | B2 | 5/2016 | Chowdury |
| 9,388,163 | B2 | 7/2016 | Hecht |
| 9,440,967 | B2 | 9/2016 | Hecht |
| 9,957,214 | B2 | 5/2018 | Madathil |
| 2004/0166553 | A1 | 8/2004 | Nguyen et al. |
| 2010/0016783 | A1 | 1/2010 | Bourke et al. |
| 2014/0127737 | A1 | 5/2014 | Kim |
| 2018/0065941 | A1 | 3/2018 | Hecht |
| 2018/0319751 | A1 | 11/2018 | Hecht |
| 2019/0185441 | A1 | 6/2019 | Hecht |

FOREIGN PATENT DOCUMENTS

| WO | 2011103536 A1 | 8/2011 |
| WO | 2012138713 A2 | 10/2012 |
| WO | 2013120081 A1 | 8/2013 |
| WO | 2014055629 A1 | 4/2014 |
| WO | 2014059158 A1 | 4/2014 |
| WO | 2016133959 A9 | 8/2016 |
| WO | 2016133995 A1 | 8/2016 |

(Continued)

OTHER PUBLICATIONS

Alam, M. P., et al. (2014). Cytoprotective pyridinol antioxidants as potential therapeutic agents for neurodegenerative and mitochondrial diseases. Bioorganic & medicinal chemistry, 22(17), 4935-4947.

(Continued)

*Primary Examiner* — Robert S Cabral
(74) *Attorney, Agent, or Firm* — Viksnins Harris Padys Malen LLP

(57) ABSTRACT

The present invention relates to the use of prodrugs susceptible to nitroreductase (NTR) activation. In particular, provided herein are mitochondria-targeting prodrug compounds and probes, including profluorescent near-infrared (NIR) probes and non-fluorescent prodrugs, as well as to methods of using said prodrug compounds and probes for imaging mitochondria and for mitochondria-specific delivery of therapeutic agents.

7 Claims, 19 Drawing Sheets

(56) References Cited

FOREIGN PATENT DOCUMENTS

| WO | 2018039077 A1 | 3/2018 |
|---|---|---|
| WO | 2018039487 A1 | 3/2018 |

OTHER PUBLICATIONS

Bae, J., et al. (2015). Nitroreductase-triggered activation of a novel caged fluorescent probe obtained from methylene blue. Chemical Communications, 51(64), 12787-12790.
Berneis, K., et al. "The enhancement of the after effect of ionizing radiation by a cytotoxic methylhydrazine derivative." European Journal of Cancer (1965) 2.1 (1966): 43-49.
Brar, Sukhdev S., et al. "Mitochondrial DNA-depleted A549 cells are resistant to bleomycin." American Journal of Physiology-Lung Cellular and Molecular Physiology 303.5 (2012): L413-L424.
Brouwer, A. M. "Standards for photoluminescence quantum yield measurements in solution (IUPAC Technical Report)." Pure and Applied Chemistry 83.12 (2011): 2213-2228.
Chandel, "Mitochondria and cancer" Cancer & Metabolism 2014, 2:8.
Chevalier, Arnaud, et al. "Selective functionalization of antimycin A through an N-transacylation reaction." Organic letters 18.10 (2016): 2395-2398.
Danson, Sarah, et al. "DT-diaphorase: a target for new anticancer drugs." Cancer treatment reviews 30.5 (2004): 437-449.
Dickinson, Bryan C., et al. "A targetable fluorescent probe for imaging hydrogen peroxide in the mitochondria of living cells." Journal of the American Chemical Society 130.30 (2008): 9638-9639.
Dodani, Sheel C., et al. "A targetable fluorescent sensor reveals that copper-deficient SCO1 and SCO2 patient cells prioritize mitochondrial copper homeostasis." Journal of the American Chemical Society 133.22 (2011): 8606-8616.
Elmes, RBP. "Bioreductive fluorescent imaging agents: applications to tumour hypoxia." Chemical Communications 52.58 (2016): 8935-8956.
Fan, Jing, et al. "Glutamine-driven oxidative phosphorylation is a major ATP source in transformed mammalian cells in both normoxia and hypoxia." Molecular systems biology 9.1 (2013): 712.
Glasauer, Andrea, et al. "Targeting antioxidants for cancer therapy." Biochemical pharmacology 92.1 (2014): 90-101.
Gorrini, Chiara, et al. "Modulation of oxidative stress as an anticancer strategy." Nature reviews Drug discovery 12.12 (2013): 931.
Gray, Michael W., et al. "Mitochondrial evolution." Science 283. 5407 (1999): 1476-1481.
Herrmann, Johannes M. "Converting bacteria to organelles: evolution of mitochondrial protein sorting." Trends in microbiology 11.2 (2003): 74-79.
Huang, Li-shar, et al. "Binding of the respiratory chain inhibitor antimycin to the mitochondrial bc1 complex: a new crystal structure reveals an altered intramolecular hydrogen-bonding pattern." Journal of molecular biology 351.3 (2005): 573-597.
Jose, Caroline, et al. "Choosing between glycolysis and oxidative phosphorylation: a tumor's dilemma?." Biochimica et Biophysica Acta (BBA)—Bioenergetics 1807.6 (2011): 552-561.
Kang, Min H., et al. "Bcl-2 inhibitors: targeting mitochondrial apoptotic pathways in cancer therapy." Clinical cancer research 15.4 (2009): 1126-1132.
Karton-Lifshin, Naama, et al. "A unique paradigm for a Turn-ON near-infrared cyanine-based probe: noninvasive intravital optical imaging of hydrogen peroxide." Journal of the American Chemical Society 133.28 (2011): 10960-10965.
Kong, Xiangxing, et al. "A Highly Selective Mitochondria-Targeting Fluorescent K+ Sensor." Angewandte Chemie International Edition 54.41 (2015): 12053-12057.
Kratz, Felix, et al. "Prodrug strategies in anticancer chemotherapy." ChemMedChem: Chemistry Enabling Drug Discovery 3.1 (2008): 20-53.
Lessene, Guillaume, et al. "BCL-2 family antagonists for cancer therapy." Nature reviews Drug discovery 7.12 (2008): 989.
Li, Yuhao, et al. "Ultrasensitive near-infrared fluorescence-enhanced probe for in vivo nitroreductase imaging." Journal of the American Chemical Society 137.19 (2015): 6407-6416.
Lim, Lori O., et al. "Mitochondrial DNA damage by bleomycin." Biochemical pharmacology 36.17 (1987): 2769-2774.
Ma, Jing, et al. "Mitochondrial targeted β-lapachone induces mitochondrial dysfunction and catastrophic vacuolization in cancer cells." Bioorganic & medicinal chemistry letters 25.21 (2015): 4828-4833.
Moreno, S. N., et al. "Reduction of nifurtimox and nitrofurantoin to free radical metabolites by rat liver mitochondria. Evidence of an outer membrane-located nitroreductase." Journal of Biological Chemistry 259.10 (1984): 6298-6305.
Redy-Keisar, Orit, et al. "Synthesis and use of QCy7-derived modular probes for the detection and imaging of biologically relevant analytes." Nature protocols 9.1 (2014): 27.
Remington's Pharmaceutical Sciences, 20th ed., Lippincott Williams & Wilkins, Baltimore, MD, 2000, p. 704.
Rin Jean, Sae, et al. "Molecular vehicles for mitochondrial chemical biology and drug delivery." ACS chemical biology 9.2 (2014): 323-333.
Sens, Rudiger, et al. "Fluorescence quantum yield of oxazine and carbazine laser dyes." Journal of Luminescence 24 (1981): 709-712.
Shen, Chuen-cheh, et al. "Repair of mitochondrial DNA damage induced by bleomycin in human cells." Mutation Research/DNA Repair 337.1 (1995): 19-23.
Smyth, Gerald E., et al. "Nitroreductase activity of NADH dehydrogenase of the respiratory redox chain." Biochemical Journal 257.3 (1989): 859-863.
Sullivan, Lucas B., et al. "Mitochondrial reactive oxygen species and cancer." Cancer & metabolism 2.1 (2014): 17.
Symons, Zoe C., et al. "Bacterial pathways for degradation of nitroaromatics." Natural product reports 23.6 (2006): 845-850.
Tzung, Shie-Pon, et al. "Antimycin A mimics a cell-death-inducing Bcl-2 homology domain 3." Nature cell biology 3.2 (2001): 183.
Wallace, Douglas C. "Mitochondria and cancer." Nature Reviews Cancer 12.10 (2012): 685.
Weinberg, Samuel E., et al. "Targeting mitochondria metabolism for cancer therapy." Nature chemical biology 11.1 (2015): 9.
Wheaton, William W., et al. "Metformin inhibits mitochondrial complex I of cancer cells to reduce tumorigenesis." elife 3 (2014): e02242.
Williams, Elsie M., et al. "Nitroreductase gene-directed enzyme prodrug therapy: insights and advances toward clinical utility." Biochemical journal 471.2 (2015): 131-153.
Xu, Zheng, et al. "Fluorescent probes for the selective detection of chemical species inside mitochondria." Chemical Communications 52.6 (2016): 1094-1119.
Yeh, Chi-Tai, et al. "A preclinical evaluation of antimycin a as a potential antilung cancer stem cell agent." Evidence-Based Complementary and Alternative Medicine 2013 (2013). Art. ID 910451.
Yuan, Lin, et al. "Development of targetable two-photon fluorescent probes to image hypochlorous acid in mitochondria and lysosome in live cell and inflamed mouse model." Journal of the American Chemical Society 137.18 (2015): 5930-5938.
Zhang et al., "Near-Infrared Molecular Probes for In Vivo Imaging" Curr Protoc Cytom. Apr. 2012; Chapter 12: Unit12.27.
Snyder, L. R. and J. J. Kirkland eds, Introduction to Modern Liquid Chromatography, 2nd Edition, John Wiley and Sons, 1979.
Stahl, E., ed. Thin Layer Chromatography, Springer-Verlag, New York, 1969.
Stahl, P. H. and Camille G. Wermuth, Eds. "Handbook of Pharmaceutical Salts: Properties, Selection, and Use," Wiley-VCH, Weinheim, 2002.
U.S. Appl. No. 16/327,287, unpublished.
Pubchem, Substance Record for SID 92763509 Create date: May 10, 2010 [retrieved on Jul. 31, 2017] <https://pubchem.ncbi.nlm.gov/substance/92763509>.
Pubchem, Substance Record for SID 164870287 Create date: Nov. 14, 2013 [retrieved on Jul. 31, 2017] <https://pubchem.ncbi.nlm.gov/substance/164870287>.

(56) References Cited

OTHER PUBLICATIONS

International Search Report from Parent PCT No. PCT/US2017/037253, dated Aug. 16, 2017, 8 pages.

Nitrobenzyl derivatives of rotenone

Nitrobenzyl derivatives of 2-methoxyestradiol

Nitrobenzyl derivatives of camptothecin

Nitrobenzyl derivatives of topotecan

Nitrobenzyl derivative of bleomycin

PRODRUG AND PROFLUORESCENT COMPOUNDS FOR SELECTIVE MITOCHONDRIAL IMAGING AND THERAPEUTIC TARGETING

CROSS-REFERENCE TO RELATED APPLICATIONS

This application is a continuation of U.S. patent application Ser. No. 16/310,305, filed Dec. 14, 2018, which represents the national stage entry of PCT International Application No. PCT/US2017/037253, filed on Jun. 13, 2017, and claims the benefit of U.S. Provisional Patent Application No. 62/350,557, filed Jun. 15, 2016, which is incorporated herein by reference as if set forth in its entirety.

STATEMENT REGARDING FEDERALLY SPONSORED RESEARCH OR DEVELOPMENT

Not applicable.

BACKGROUND

Mitochondria are intracellular organelles responsible for a number of metabolic transformations and regulatory functions. They produce most of the ATP employed by eukaryotic cells. They are also the major source of free radicals and reactive oxygen species (ROS) that cause oxidative stress. Recent publications have the described the potential importance of mitochondrial targeting for the development of new therapeutic agents such as anticancer agents.[1] For example, the selective induction of elevated ROS levels in mitochondria has been found to produce different effects in cancer cells than in normal cells.[1] Several types of agents which affect mitochondrial function have been the focus of preclinical studies,[2] which argues for the relevance of this strategy. While mitochondrial localization has been reported for numerous molecules,[3] notably those containing a lipophilic cation,[4] incorporating a mitochondrial targeting moiety within a molecule may prove challenging in the broader context of molecular design for a specific cellular target.

Therefore, there remains a need in the art for improved tools for imaging mitochondria and for specifically targeting therapeutic agents to mitochondria.

BRIEF SUMMARY

The present invention relates to the use of prodrugs susceptible to nitroreductase (NTR) activation. In particular, provided herein are mitochondria-targeting prodrug compounds and probes, including profluorescent near-infrared (NIR) probes, as well as methods of using said prodrug compounds and probes for imaging mitochondria and for mitochondria-specific delivery of therapeutic agents.

In a first aspect, provided herein is a prodrug compound having a formula selected from the group consisting of:

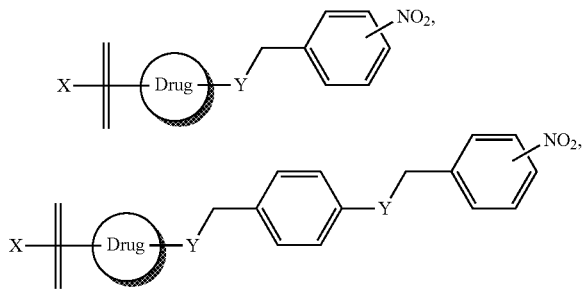

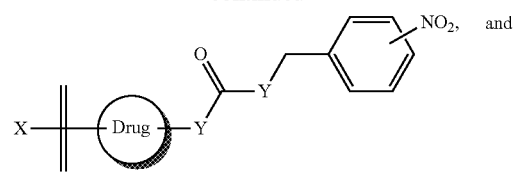

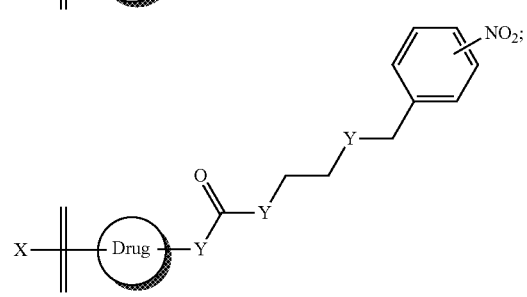

wherein X is selected from the group consisting of an alkylammonium group ($NR_3^+$), $PR_3^+$, H, and an alkyl group, wherein Y is selected from the group consisting of O, NR, and S; wherein R is selected from the group consisting of H, an alkyl group, and an aromatic group; and wherein Drug represents any active drug having an alkylable heteroatom.

In another aspect, provided herein is a prodrug compound having a formula selected from the group consisting of:

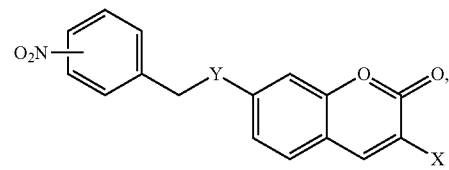

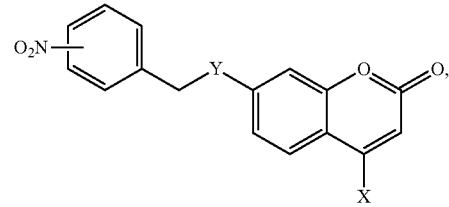

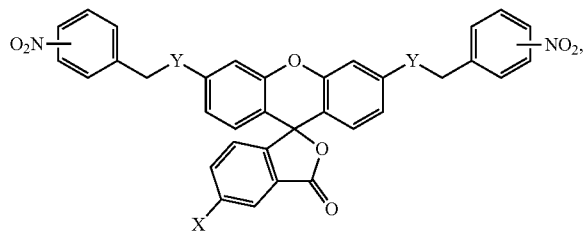

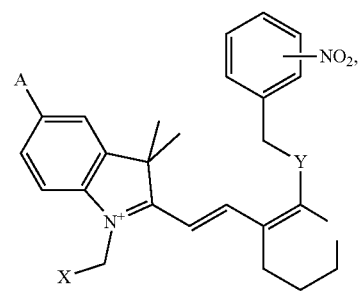

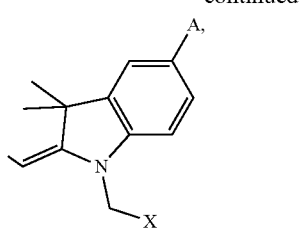

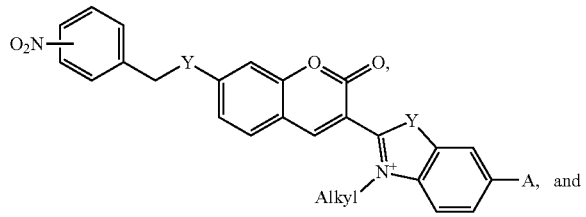

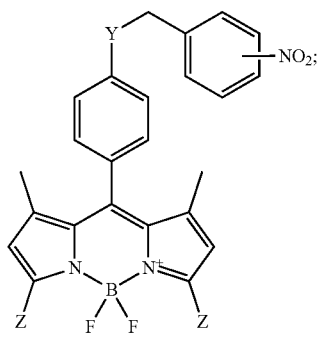

wherein Z is an alkyl or styryl group, wherein A is H, SO$_3$H, or SO$_3$K; and wherein X is NR$_3^+$, PR$_3^+$, H, or an alkyl group.

A profluorescent compound having a formula selected from the group consisting of:

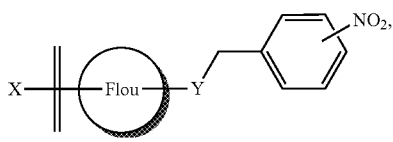

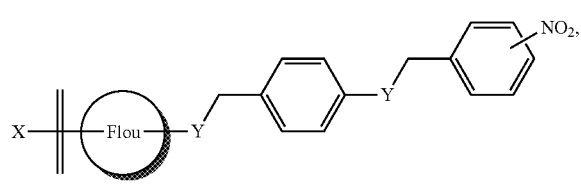

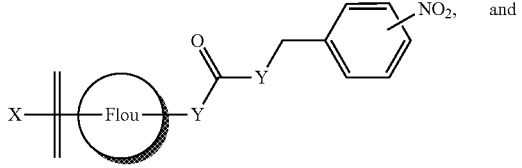

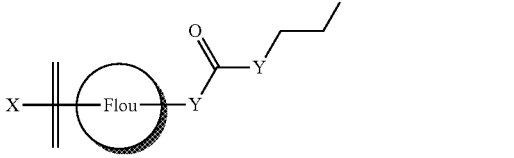

wherein X is selected from the group consisting of an alkylammonium group (NR$_3^+$), PR$_3^+$, H, and an Alkyl group, wherein Y is selected from the group consisting of O, NR, and S; wherein R is selected from the group consisting of H, an alkyl group, and an aromatic group; and wherein Fluo represents any fluorescent compound having an alkylatable heteroatom.

In a further aspect, provided herein is a profluorescent compound having the formula, or an ortho-substituted analogue thereof:

wherein R$_1$ and R$_3$ are independently H, aryl or alkyl groups, and R$_2$ is an acyl group or a group chemically modifiable to an acyl group.

In yet another aspect, provided herein is a pharmaceutical composition comprising a prodrug or profluorescent compound as described herein and a pharmaceutically acceptable carrier.

Also provided herein is a method for imaging mitrochondria, where the method comprises contacting the compound of any one of claims 1-4 to a target cell; and detecting a nitrobenzyl fluorescence signal in one or more mitochondria of the cell.

In another aspect, provided herein is a method for selective delivery of a therapeutic agent to a mitochondrion of target cell, the method comprising contacting a target cell to a prodrug or profluorescent compound operably linked to a therapeutic agent, whereby the therapeutic agent is selectively activated upon entry to a mitochondrion of target cell.

BRIEF DESCRIPTION OF THE DRAWINGS

The present invention will be better understood and features, aspects, and advantages other than those set forth above will become apparent when consideration is given to the following detailed description thereof. Such detailed description makes reference to the following drawings, wherein.

DETAILED DESCRIPTION

All publications, including but not limited to patents and patent applications, cited in this specification are herein incorporated by reference as though set forth in their entirety in the present application.

The compounds, compositions, and methods provided herein are based at least in part on the present inventors' discovery of nitroreductase activity in mitochondria. It was further discovered that nitroreductase converts novel prodrugs of the mitochondrial poison, antimycin A, into a fluorescent, detectable compound upon entry into a mitochondrion. Without limitation, the present invention exploits the discovery that, upon, delivery of the prodrug to mitochondria of a target cell, it is converted to AMA by the mitochondrial nitroreductase and exhibits increased cytotoxicity relative to AMA administered alone. Accordingly, provided herein are prodrugs susceptible to nitroreductase (NTR) activation, and compounds and methods for specific mitochondrial imaging and for selective delivery of therapeutic agents. In particular, provided herein are mitochondria-targeting prodrug compounds and probes, including profluorescent near-infrared (NIR) probes, as well as to methods of using said prodrug compounds and probes for imaging mitochondria and for mitochondria-specific delivery of therapeutic agents.

I. Compounds and Compositions

Accordingly, in a first aspect, provided herein is a prodrug form of a mitochondria-targeting compound, including compounds known to impact mitochondrial function. Preferably, the compound is susceptible to nitroreductase (NTR) activation in mitochondria. As used herein, the term "prodrug" refers to compounds that are transformed (typically rapidly) in vivo to yield the parent compound of the above formulae, for example, by enzymatic conversion in mitochondria. Synthesis of prodrug forms of such mitochondria-targeting agents will generally involve modifying a heteroatom (usually oxygen) by alkylation with a nitrobenzyl group. As used herein, the term "mitochondria-targeting" refers to agents that modulate mitochondrial activity in vivo or in vitro, and includes drugs or chemical that be specifically delivered into mitochondria using, for example, conjugation to lipophilic cations or liposomes.

Figure 1:
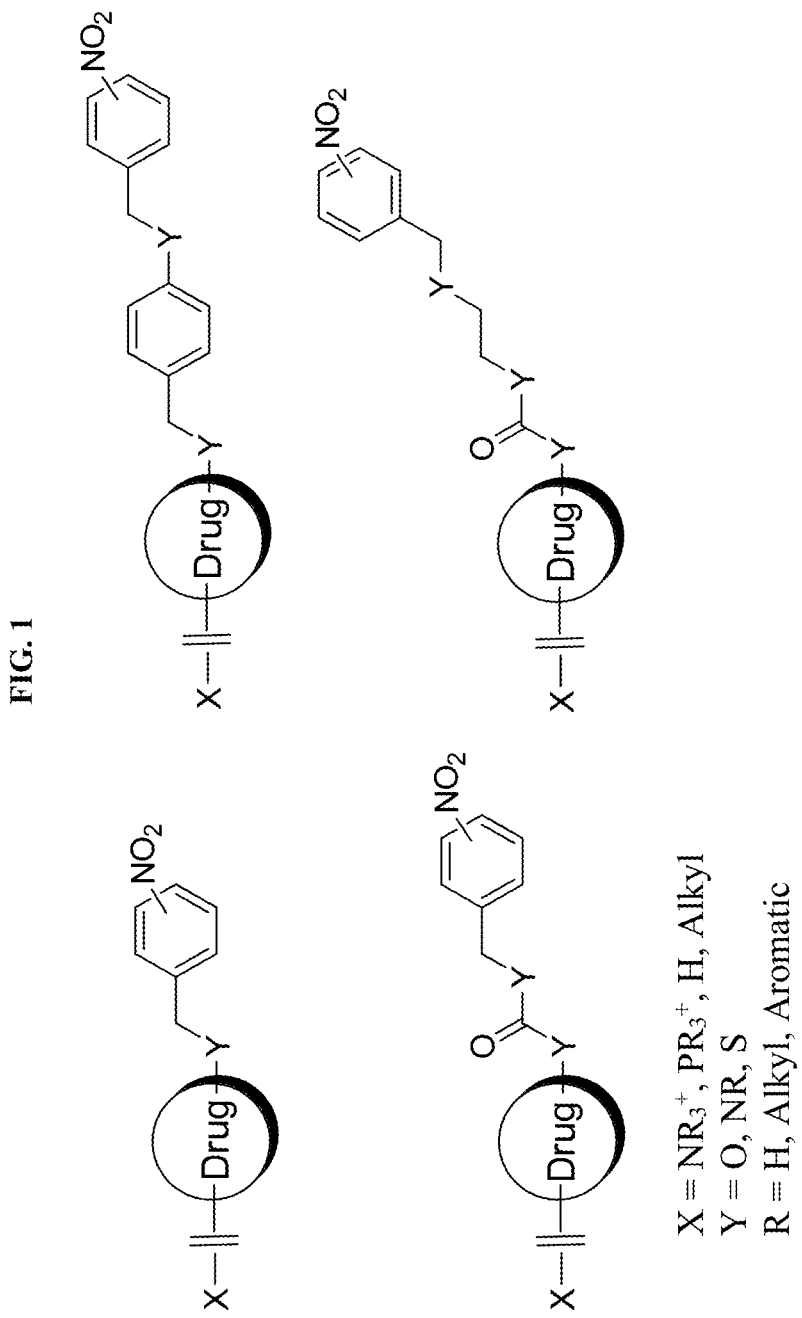
FIG. 1 presents representative strategies for the release of active drug depending of the use of a direct alkylation incorporating an ortho-nitrobenyl or para-nitrobenzyl motif or through the introduction of self immolative linkers.
Figure 2:
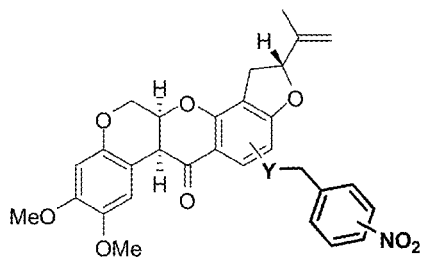
FIG. 2 presents chemical structures of exemplary prodrug forms of mitochondria-targeting agents. Any drug exhibiting an alkylable heteroatom is suitable for design and use as a prodrug as provided in this document.
Figure 2:
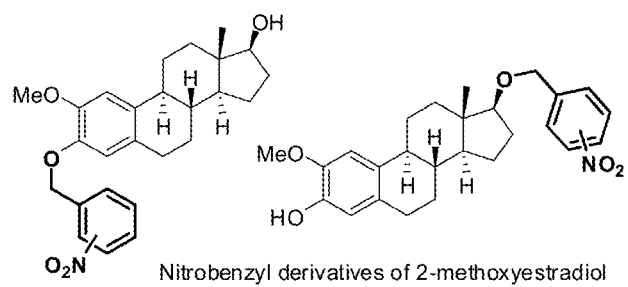
Figure 2:
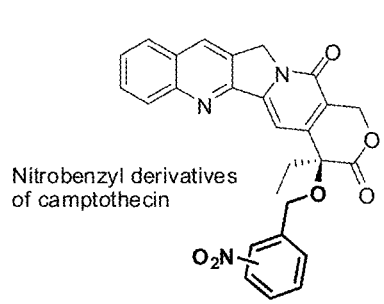
Figure 2:
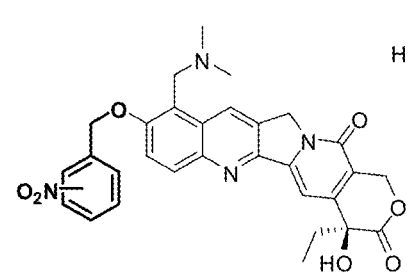
Figure 2:
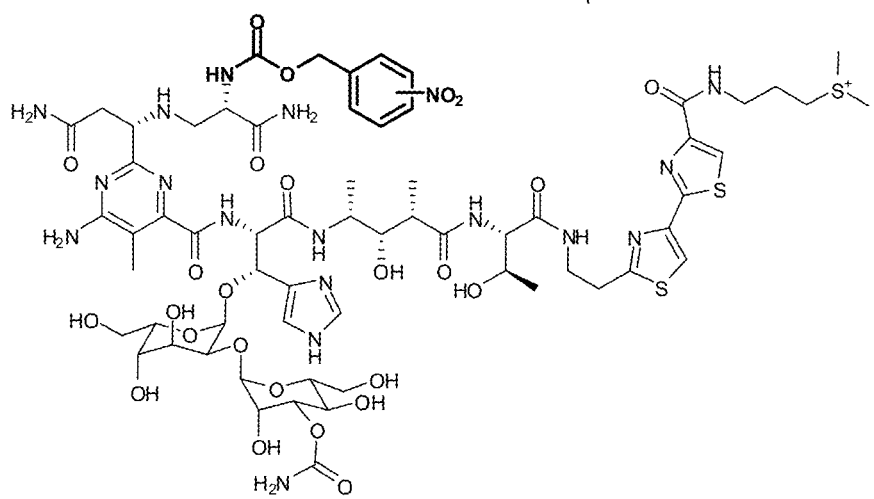

In exemplary embodiments, compounds of the invention are prodrugs releasable with nitroreductase. Without being bound to any particular mechanism or theory, delivery of such prodrugs into mitochondria permits mitochondria-specific release and activity of their active drug forms. As shown in FIG. 1, strategies for synthesizing prodrug forms of active drugs involve a direct alkylation incorporating a ortho-nitrobenyl or para-nitrobenzyl motif or the introduction of self immolative linkers. Chemical structures of exemplary prodrug forms of putative mitochondria-targeting agents as set forth in FIG. 2. Any drug exhibiting an alkylatable heteroatom is suitable for design and use as a prodrug as provided in this document.

Figure 18:
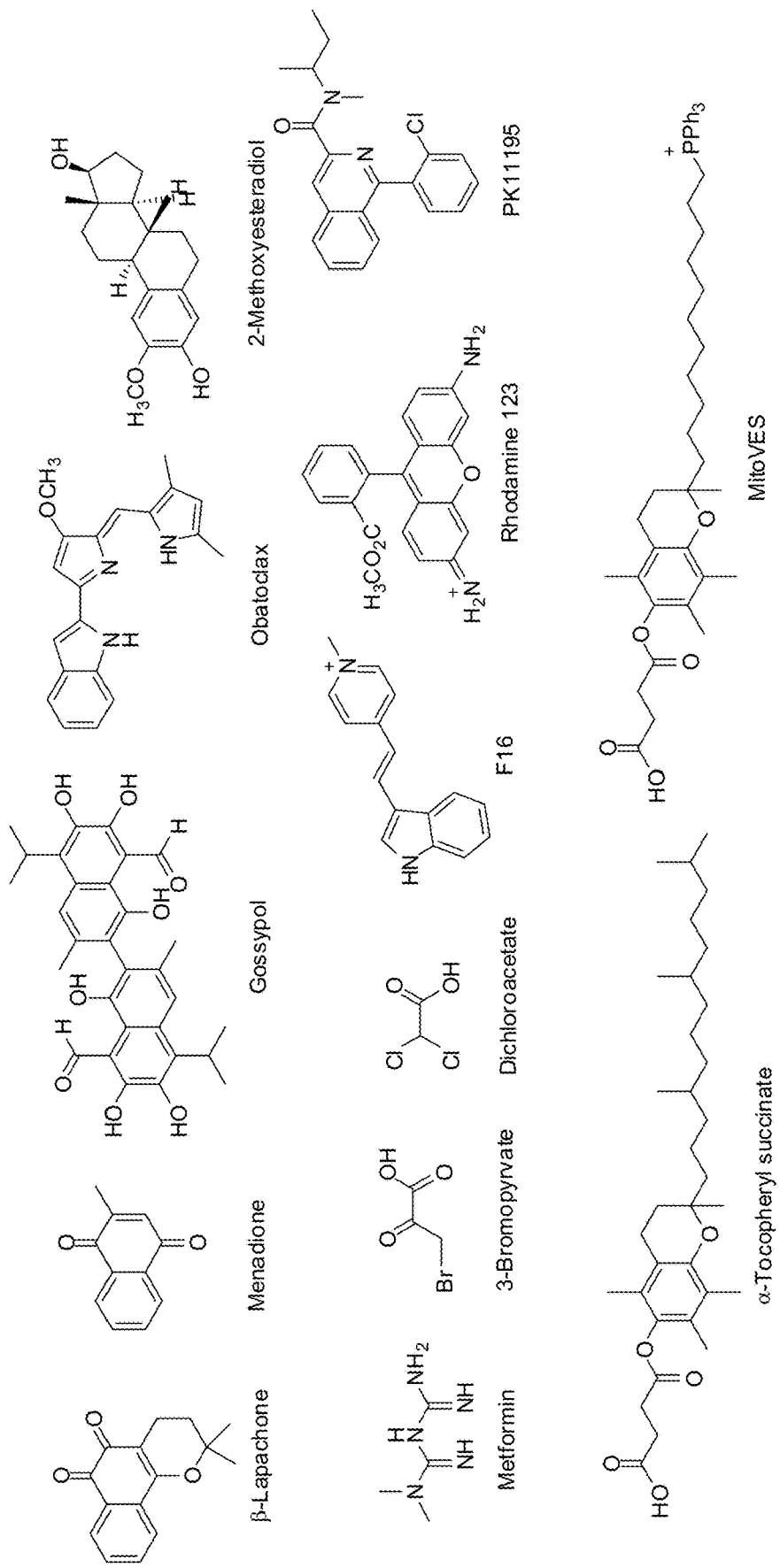
FIG. 18 presents chemical structures of mitochondria-targeting anticancer agents useful for prodrug compounds according to the invention.

In some cases, compounds of the invention are prodrug forms of mitochondria-targeting anticancer agents. Several classes of mitochondrial targeted anticancer agents, known as 'mitocans', have been reported and categorized into eight classes depending on their sites of action, including (1) hexokinase inhibitors; (2) Bcl-2 family protein ligands; (3) thiol redox system disruptors; (4) mitochondrial membrane transporter/channel inhibitors; (5) electron transfer chain deregulators; (6) inner mitochondrial membrane disruptors; (7) TCA cycle inhibitors; and (8) mtDNA damaging agents. See, for review and exemplary chemical formulas of mitochans, Ma et al., *Bioorganic & Medicinal Chemistry Letters* 25 (2015) 4828-4833. Exemplary mitocans are presented in FIG. 18.

Figure 3:
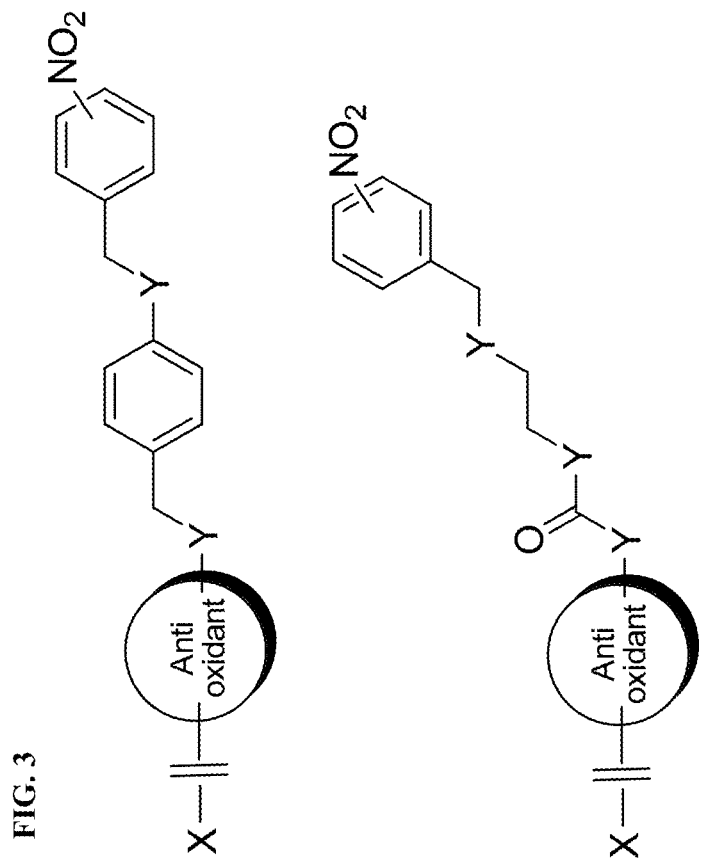
FIG. 3 representative strategies for the release of active antioxidant depending of the use of a direct alkylation incorporating an ortho-nitrobenyl or para-nitrobenzyl motif or through the introduction of self immolative linkers.
Figure 3:
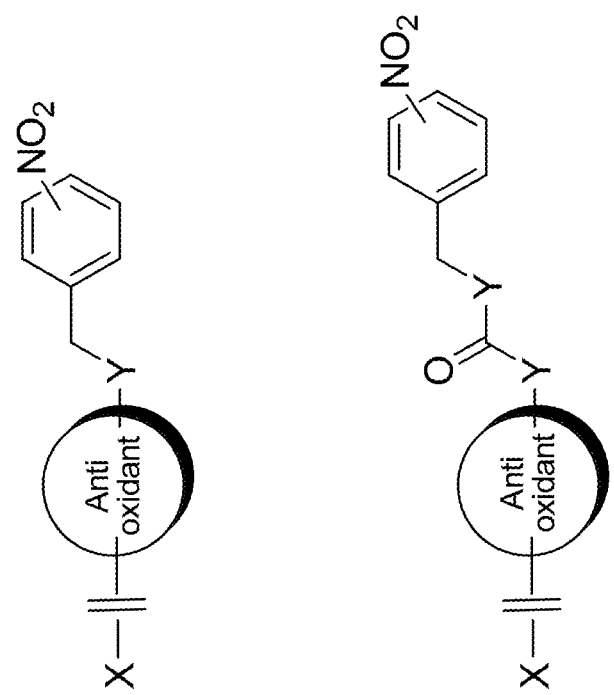
Figure 4:
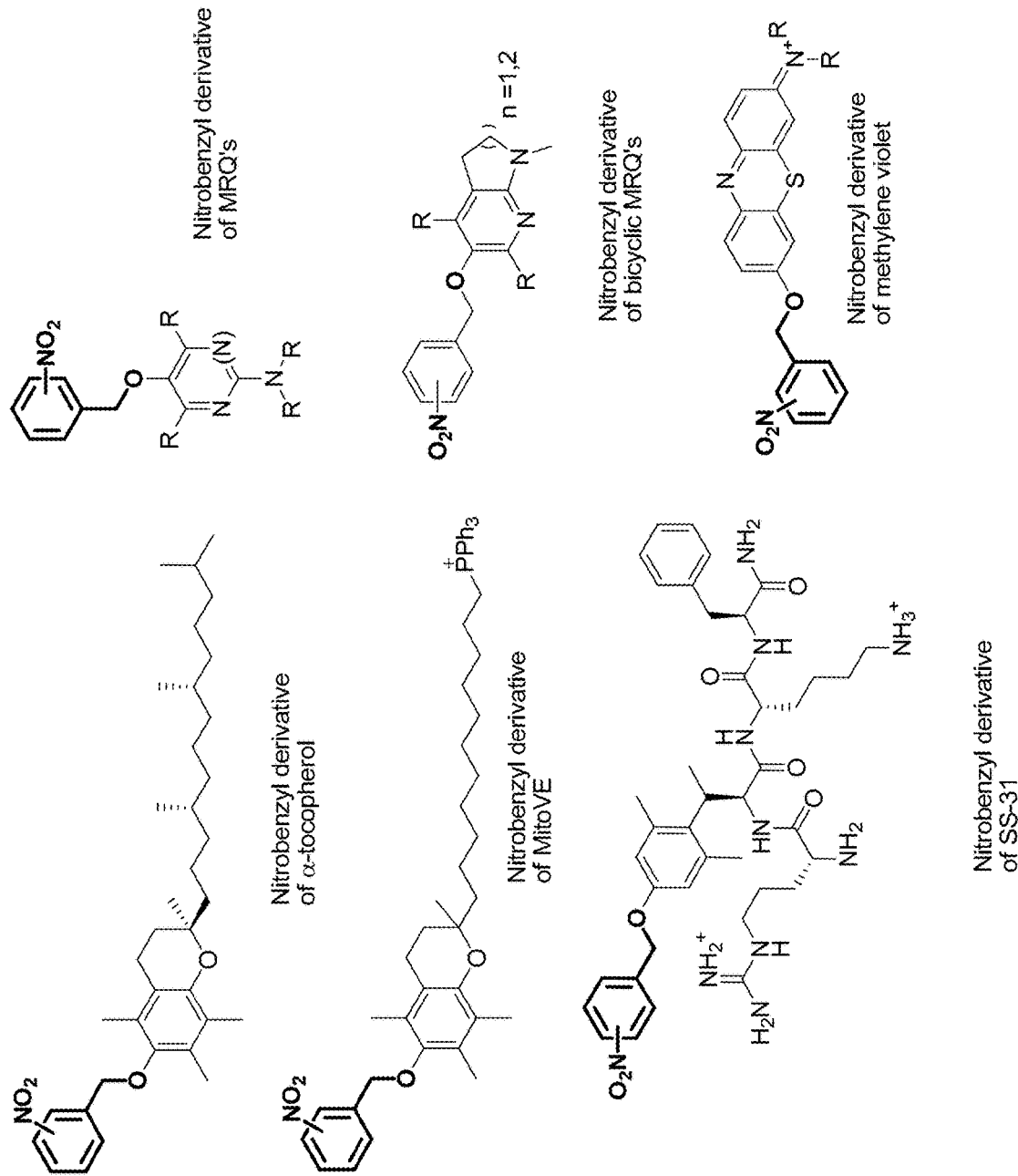
FIG. 4 presents chemical structures of exemplary prodrug forms of mitochondria-targeting antioxidants. Any antioxidant exhibiting an alkylable heteroatom is suitable for design and use as a prodrug as provided in this document.

In some cases, compounds of the invention are prodrug forms of antioxidants including mitochondria-targeting antioxidants. For example, referring to FIG. 3, prodrug forms of antioxidants can be synthesized using direct alkylation for incorporation of an ortho-nitrobenyl or para-nitrobenzyl motif, or through the introduction of self-immolative linkers. Exemplary prodrug mitochondria-targeting antioxidants include, without limitation, compounds having the structures shown in FIG. 4. As described herein, any drug exhibiting an alkylable heteroatom is suitable for synthesis and use as a prodrug as provided in this document.

In a preferred embodiment, provided herein is a prodrug form of antimycin A (AMA). The prodrug form of AMA is a profluorescent probe, meaning that the compound serves as a molecular probe comprising a caged fluorochrome. As used herein, the term "caged fluorochrome" refers to a nonfluorescent chemical compound that becomes fluorescent upon activation or unmasking. While AMA is fluorescent, the profluorescent probes described herein are not fluorescent in the absence of mitochondrial nitroreductase activity. Without being bound to any particular mechanism or mode of action, it is believed that mitochondrial nitroreductase activity catalyzes the conversion of the prodrug to AMA and "unmasks" a detectable fluorescent probe by enzymatic reduction of a nitro group. It will be appreciated, however, that the released drug need not be fluorescent to exert its therapeutic effects. Compounds of the invention also encompass prodrug forms of non-fluorescent compounds.

In some cases, the profluorescent probes provided herein are profluorescent near infrared (NIR) compounds that are alkylated derivatives of AMA. In some cases, the profluorescent probe has the following chemical formula:

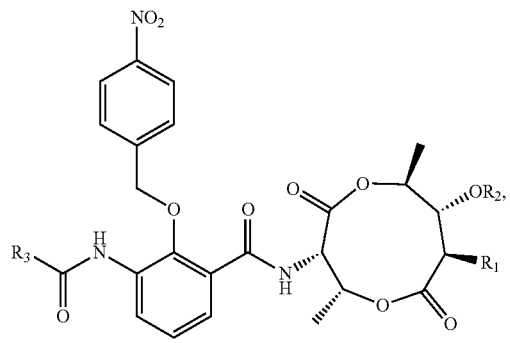

(Formula 4a)

For Formula 4a, $R_1$ and $R_3$ are independently H, aryl or alkyl groups, including, including short linear and branched alkyl groups having 1 to 10 carbon atoms (with substitutions). As used herein, an "alkyl group" means a linear, branched, or cyclic saturated hydrocarbon. Preferably, an alkyl group has between one and six carbon atoms. An alkoxy group also refers to substituted alkyl groups, which may include substituents such as alkanoyloxy groups, alkenyl groups, alkoxy groups, alkylsilyl groups, alkylsulfonyl groups, alkylsulfoxy groups, alkylthio groups, alkynyl groups, amino groups such as mono- and di-alkylamino groups and mono- and di-arylamino groups, amide groups, aryl groups, arylalkyl groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combinations of these. Preferred substituents are alkoxy groups, amino groups such as dialkylamino groups, diarylamino groups, carboxylic acid-containing groups, haloalkyl groups, halogens, hydroxyl groups, nitrile groups, nitro groups, and sulfonic acid groups. Examples of preferred alkyl groups include, but are not limited to, methyl, ethyl, propyl, isopropyl, cyclopropyl, n-butyl, isobutyl, sec-butyl, tert-butyl, cyclobutyl, pentyl, isopentyl, neo-pentyl, 1-ethylpropyl, cyclopentyl, hexyl, and cyclohexyl. As used herein, a "halogen" means fluorine, chlorine, bromine, and/or iodide.

For Formula 4a, $R_2$ is an acyl group (RCO—, where R represents an alkyl group that is linked to the carbon atom of the group by a single bond) such as a formyl, acetyl, propionyl, benzoyl, or acrylyl group. $R_2$ also can be a group that is modifiable to any acyl group. As used herein, an "acyl group" means a linear, branched, or cyclic substituent having a carbonyl group which is attached to either an oxygen atom, e.g., of a hydroxyl group, or a nitrogen atom, e.g., of an amino group. An acyl group can include an alkoxy group, an alkyl group, an aryl group, an arylalkyl group, an ester group, an ether group a heterocyclic group, a vinyl group, and combinations thereof. An acyl group also may be substituted with substituents such as alkanoyloxy groups, alkenyl groups, alkylsilyl groups, alkylsulfonyl groups, alkylsulfoxy groups, alkylthio groups, alkynyl groups, amino groups such as mono- and di-alkylamino groups and mono- and di-arylamino groups, amide groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combination of these. It should be understood that an acyl group also can be an amino protecting group or a hydroxyl protecting group. As a hydroxyl protecting group, an acyl group may form an ester or carbonate. As an amino protecting group, an acyl group may form an amide or a carbamate. Examples of acyl groups include, but are not limited to, alkoyl groups, aroyl groups, arylalkoyl groups, vinoyl groups. Preferred acyl groups are benzoyl, ethanoyl, tigloyl, or 2-methyl-2-butenoyl, 2-methyl-1-propenoyl, hexanoyl, butyrl, 2-methylbutyryl, phenylacetyl, propanoyl, furoyl, and tert-butyloxycarbonyl.

In some cases, the compound is an ortho-substituted analogue of Formula 4a.

In another aspect, provided herein are compounds that are profluorescent forms of dyes for use in the near-infrared (NIR) wavelengths between 700 and 900 nm. Such compounds are useful for nitroreductase detection in mitochondria. Furthermore, molecular probes that emit light in the NIR region are particularly suited for in vivo and in vitro imaging. As profluorescent forms, the compounds provided herein are useful for specific targeting of biomolecules of interest and reporting of molecular processes through fluorescence activation. General structures of profluorescent probes for nitroreductase detection in mitochondria include the following:

where X=NR$_3^+$, PR$_3^+$ H, Alkyl;
Y=O, NR, S; and
R=H, Alkyl, Aromatic.

The four schemes represent four strategies for the elimination of active fluorescent dye depending of the use of a direct alkylation incorporating a ortho-nitrobenyl or para-nitrobenzyl motif, or through the introduction of self-immolative linkers.

Compounds of the invention also include profluorescent forms of dyes for use in the entire range of the UV/visible light spectrum such as, for example, coumarins (and hybrids and derivatives thereof), xanthene fluorophores (e.g., rhodamin and fluoresceins), BODIPY, cyanine dyes, NIR fluorescent cyanine dyes, squaraine, and tetrapyrrole-based compounds, such as hematoporphyrin (HpD), meso-tetra-m-hydroxyphenylchlorin (m-THPC), benzoporphyrin derivatives (BPD), and sulfonated phthalocyanines. See, e.g., Zhang et al., *Curr Protoc Cytom.* 2012 April; Chapter 12:Unit12.27. Synthesis of prodrug, profluorescent forms of such near-infrared dyes will generally involve modifying a heteroatom (usually oxygen) by alkylation with a nitrobenzyl group. In some cases, compounds are profluorescent forms of reactive oxygen species (ROS)-activated near-infrared fluorescent dyes. Exemplary compounds derived from known fluorophores structure include the following:

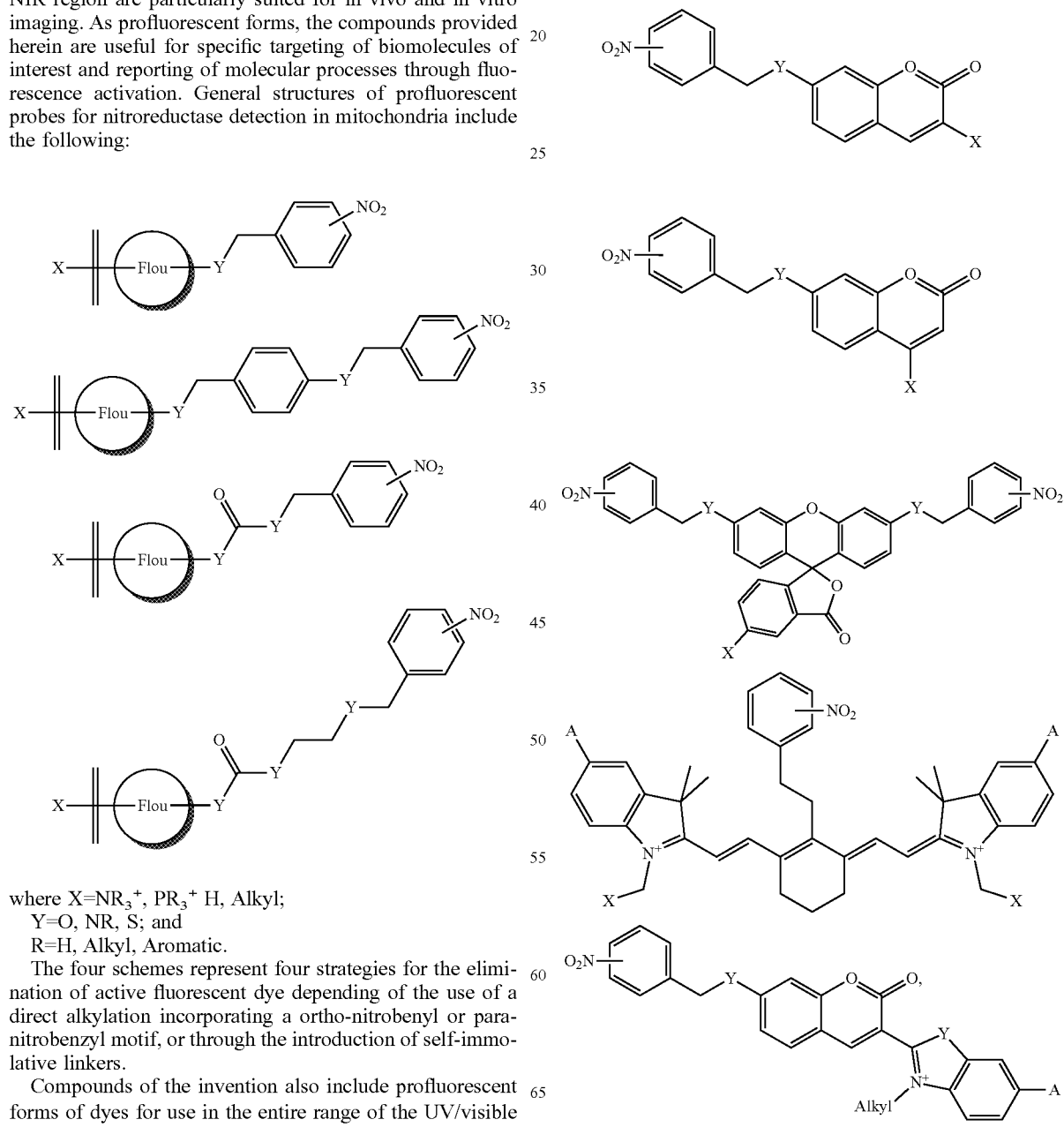

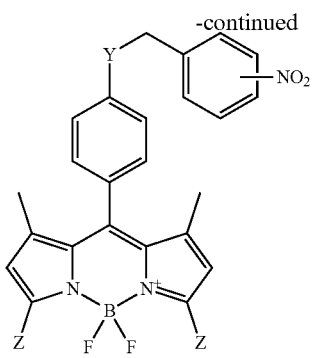

where: Z=Alkyl, Styryl;
A=H, SO$_3$H, SO$_3$K; and
X=NR$_3^+$, PR$_3^+$, H, Alkyl.

It is to be noted that the styryl group may be either a styryl group not having a substituent, or a styryl group having a substituent. Likewise, the alkyl group may be either an alkyl group not having a substituent, or an alkyl group having a substituent.

The compounds of the invention are synthesized by an appropriate combination of generally well-known synthetic methods. Techniques useful in synthesizing the compounds of the invention are both readily apparent and accessible to those of skill in the relevant art. Exemplary synthetic schemes leading to a probe of the invention is set forth in the scheme in FIG. 10 and described in the Examples section below. These examples illustrate certain of the diverse methods available for use in assembling the compounds of the invention, it is not intended to limit the scope of reactions or reaction sequences that are useful in preparing the compounds of the present invention.

Also provided herein are pharmaceutically acceptable salts of profluorescent probes. As used herein, the term "pharmaceutically acceptable salt" refers to derivatives of the compounds described herein, wherein the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

Profluorescent compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

II. Methods of Use

The compounds of the invention are useful as probes, indicators, drugs, and the like. For example, a profluorescent compound can be used as a detectable marker of mitochondria for applications such as imaging of live cells. In some cases, the method comprises contacting a target cell to a profluorescent compound and exposing the target cell to light at a wavelength that is excitatory for a selected fluorochrome, and detecting a fluorescence emission, if present. Upon conversion, the profluorescent compounds described herein exhibit an emission wavelength in the NIR region, which affords good cell imaging efficiency by diminishing the background and enhancing light penetrability. The presence of fluorescence emission at the expected wavelength is an indicator that mitochondrial nitroreductase activity converted the profluorescent compound to AMA. It may be noted further that non-fluorescent prodrugs of mitochondrially active compounds may be delivered selectively to mitochondria in their active form by the localized action of a mitochondrial nitroreductase.

In some cases, the method comprises contacting a living target cell to a profluorescent compound provided to the cell in a suitable culture medium. For live cell imaging, the contacted cell can be analyzed on an inverted fluorescence microscope. Preferably, a heated stage is used to maintain the cells at a suitable temperature. The suitable culture medium and a suitable stage temperature will depend on the type of cell being viewed, and can be readily determined by one of ordinary skill in the art. For long observation times involving cultured mammalian cells, it can be advantageous to chamber the microscope in 5% CO$_2$ to maintain cell viability. For example, as described in the Examples for compound 4a, A549 cells (adenocarcinomic human alveolar basal epithelial cells) were cultured in RPMI-1640 medium at 37° C. in 5% CO$_2$, a useful concentration of 4a for imaging applications was 25 and the observation time was 4 hours.

Digital imaging fluorescence microscopy is known in the art. Complete digital imaging fluorescence microscopy systems, or components for assembly of a complete system, are commercially available. Generally, a basic digital imaging fluorescence microscopy system includes the following operationally linked components: (1) a conventional fluorescence microscope, (2) a means for optical sectioning, e.g., a micrometer, (3) an optical detector, e.g., a CCD camera, and (4) a computer or other storage medium to store optical data. The foregoing basic components are commercially available. The operational linkage of the basic components is within ordinary skill in the art. Moreover, complete digital imaging fluorescence microscopy systems are commercially available (e.g., Scanalytics, Billerica, Mass.).

III. Therapeutic Applications

The profluorescent compounds provided herein are useful for specific targeting of therapeutic agents to mitochondria of a target cell. Accordingly, in another aspect, the present invention provides methods for treating a target cell or subject by administering a therapeutically effective amount of a pharmaceutical composition comprising a profluorescent compound and a pharmaceutically acceptable carrier. As used herein, the term "treating" includes partially or completely alleviates, ameliorates, relieves, inhibits, delays onset of, reduces severity of and/or reduces incidence of one or more symptoms or features of a particular disease, disorder, and/or condition, and/or preventing or eliminating said symptoms. As used herein, the term "treating" indicates an improvement, increase, or reduction in values that are relative to a baseline measurement, such as a measurement in the same individual prior to initiation of the treatment described herein, or a measurement in a control individual (or multiple control individuals) in the absence of the treatment described herein. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

"Subject" refers to a warm blooded animal such as a mammal, preferably a human, or a human child, which is afflicted with, or has the potential to be afflicted with one or more diseases and disorders described herein.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

The methods can be used to treat or suppress conditions including but not limited to cancer, obesity, atherosclerosis, amyotrophic lateral sclerosis, Parkinson's Disease, heart failure, myocardial infarction (MI), Alzheimer's Disease, Huntington's Disease, schizophrenia, bipolar disorder, fragile X syndrome, chronic fatigue syndrome, and Leigh syndrome, in a subject by administering an effective amount of a compound as described above including a salt or solvate or stereoisomer thereof.

For therapeutic methods, the profluorescent compounds provided herein are preferably formulated as compositions comprising one or more additional active agents. For example, a profluorescent probe can be operably linked to one or more active agents. As used herein, the term "operably linked" refers to a juxtaposition wherein the components are configured so as to perform their usual function. For example, a mitochondria specific compound operably linked to therapeutic agent will direct the linked agent to be localized to the mitochondria. Without being bound to any particular mechanism or mode of action, it is believed that mitochondrial nitroreductase activity catalyzes the conversion of the profluorescent compound to AMA and "unmasks" a detectable fluorescent probe and selectively releases or activates the active agent for mitochondria-specific activity. The linked agent maintains biological activity in the mitochondria. Suitable classes of active agents include, but are not limited to, antibiotic agents, antimicrobial agents, anti-acne agents, antibacterial agents, antifungal agents, antiviral agents, steroidal anti-inflammatory agents, nonsteroidal anti-inflammatory agents, anesthetic agents, antipruriginous agents, antiprotozoal agents, antioxidants, antihistamines, vitamins, and hormones.

In a particular embodiment, the therapeutic method is a method for treating cancer in a subject in need thereof. The profluorescent compounds described herein have increased toxicity toward cancer cells relative to antimycin A (AMA). In some cases, the method comprising contacting a target cell to a profluorescent compound described herein. The compound can be contacted to the target cell at a concentration between about 0.5 µM and 20 µM (e.g., about 0.5, 0.75, 1, 1.5, 2, 2.5, 5, 7.5, 10, 15, 20 µM). In exemplary embodiments, the method comprising about 1 µM to about 10 µM concentrations of a profluorescent compound.

In some cases, the therapeutic method is a method for treating a disorder or condition associated with a mitochondrial dysfunction. Suitable mitochondrial disorders that can be treated with the compositions disclosed herein include but are not limited to mitochondrial myopathies. Mitochondrial myopathies include Kearns-Sayre syndrome, Leigh's syndrome, mitochondrial DNA depletion syndrome (MDS), mitochondrial encephalomyopathy, lactic acidosis and strokelike episodes (MELAS), myoclonus epilepsy with ragged red fibers (MERRF), mitochondrial neurogastrointestinal encephalomyopathy (MNGIE), neuropathy, ataxia and retinitis pigmentosa (NARP), and progressive external ophthalmoplegia (PEO).

Mitochondria also represent an attractive target for cancer chemotherapy due to differences in mitochondrial utilization by normal and malignant cells. See, e.g., Glasauer and Chandel, *Biochemical Pharmacology* 92 (2014) 90-101; Sullivan and Chandel, *Cancer & Metabolism* 2014, 2:17; Gorrini et al., *Nat. Reviews* 2013, 12:931; Jose et al., *Biochimica et Biophysica Acta* 1807 (2011) 552-561; Chandel, *Cancer & Metabolism* 2014, 2:8; Fan et al., *Molecular Systems Biology* 2013, 9:712; and Wheaton et al., *eLife* 2014; 3:e02242. Since the delivery of anticancer agents selectively to tumor cells represents a therapeutic challenge of long standing, the selective activation of prodrugs of such compounds in the mitochondria hold the potential for dramatically improved therapeutic outcomes. Exemplary compounds for as mitochondria-targeting therapeutic agents as prodrugs include, without limitation, bleomycin (see, e.g., Lim et al., *Biochem. Pharmacol.*, 36, 2769-2774 (1987); Shen et al., *Mutat. Res.*, 337, 19-23 (1995); and Brar et al., *Am. J. Physiol.*, 303, L413-L424 (2012)), metformin, procarbazine (Berneis et al., *European Journal of Cancer* 1966; 2:43-9), and the compounds set forth in FIG. 2. Other anti-cancer agents compounds include those that promote ROS production and, therefore, irreversible oxidative damage in tumor cells such as Arsenic trioxide (ATO), Elesclomol (STA-4783), rituximab, the piperidine derivative lanperisone, and the ROS-producing azo derivative of procarbazine. See, for review, Glasauer and Chandel, *Biochemical Pharmacology* 92 (2014) 90-101.

Formulations containing one or more of the compounds described herein may be prepared using a pharmaceutically acceptable carrier composed of materials that are considered safe and effective and may be administered to an individual without causing undesirable biological side effects or unwanted interactions. As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Pharmaceutical compositions including the disclosed compounds are provided. The pharmaceutical compositions may be for administration by oral, parenteral (intramuscular, intraperitoneal, intravenous (IV) or subcutaneous injection), transdermal (either passively or using iontophoresis or electroporation), transmucosal (nasal, vaginal, rectal, or sublingual) routes of administration or using bioerodible inserts and can be formulated in dosage forms appropriate for each route of administration. In a preferred embodiment, the compounds are administered orally. In another embodiment, the compounds are administered parenterally in an aqueous solution.

The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower.

EXAMPLES

Reference is now made to the following examples, which together with the above descriptions illustrate the invention in a non-limiting fashion.

Example 1: Mitochondrial Nitroreductase Activity Enables Selective Imaging and Therapeutic Targeting Nitroreductase activities have been known for decades, studied extensively in bacteria, and also in systems as diverse as yeast, trypanosomes and hypoxic tumors. The putative bacterial origin of mitochondria prompted us to explore the possible existence of nitroreductase activity within this organelle, and to probe its behavior in a cellular context. Presently, by the use of a profluorescent near infrared (NIR) dye, we characterize the nature of a nitroreductase activity localized in mammalian cell mitochondria.

Figures 5A, 5B:
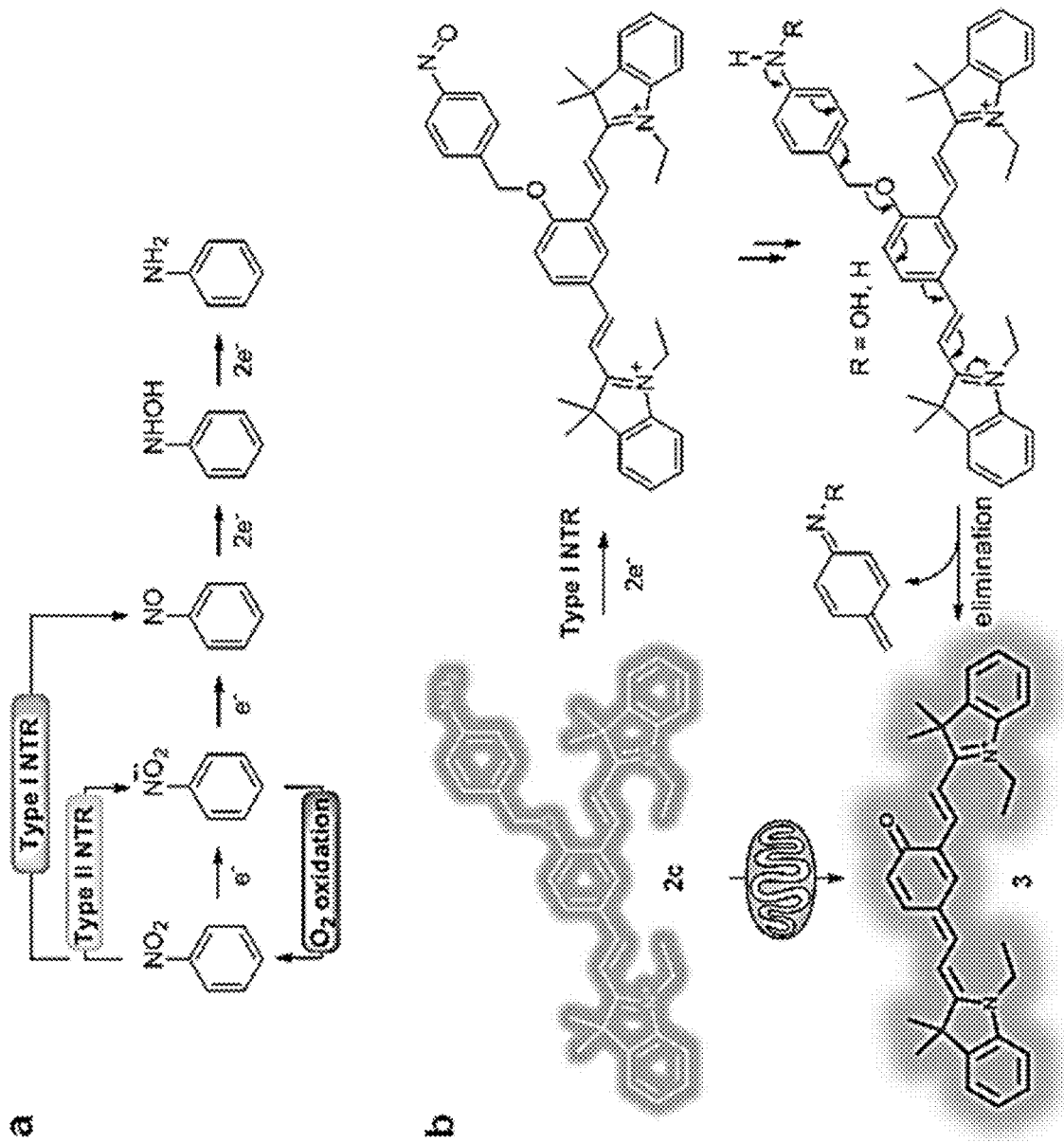
FIGS. 5A-5B set forth exemplary mechanisms for nitroreductase (NTR) activation of fluorophore 3. (a) General mechanisms proposed for type I and type II nitroreductases. (b) Mechanism of type I nitroreductase reduction applied to the activation of probe 2c.

An alternative strategy might involve the organelle-specific enzymatic activation of an inactive prodrug,[5] e.g., by an enzymatic activity abundant within the organelle.[6] The generally accepted bacterial origin of mitochondria[7] led us to investigate bacterial enzymatic activities of potential utility for mitochondrial prodrug activation. The presence of redox enzymes in bacteria is now well established,[8] and bacterial nitroreductase has been reported to reduce nitroaryl compounds to the corresponding (hydroxy)anilines, apparently by one of two mechanisms.[9] One of these (type I) involves an initial two-electron reduction of nitro groups and is tolerant of oxygen, permitting nitro group reduction to proceed to completion (FIG. 5a). Type II nitroreductase, in contrast, involves an initial one-electron reduction and proceeds to completion only under hypoxic conditions.[9] While nitroreductase activity in human cells appears to have been reported thus far only in hypoxic tumors,[10] early reports of nitroreductase activity in mitochondrial fractions isolated from mammalian liver cells[11] suggested the possible existence of a type I mitochondrial nitroreductase activity.

The detection of nitroreductase activities within hypoxic tumor tissue using fluorogenic methods has been described recently, as reviewed by Elmes,[12] and these presumably involve type II nitroreductase. Fluorescent probes have also been designed to measure small chemical species within mitochiondria.[4,13] In comparison, there appears to have been no enzymatic activity detected in mitochondria using a fluorogenic method.

Figure 10:
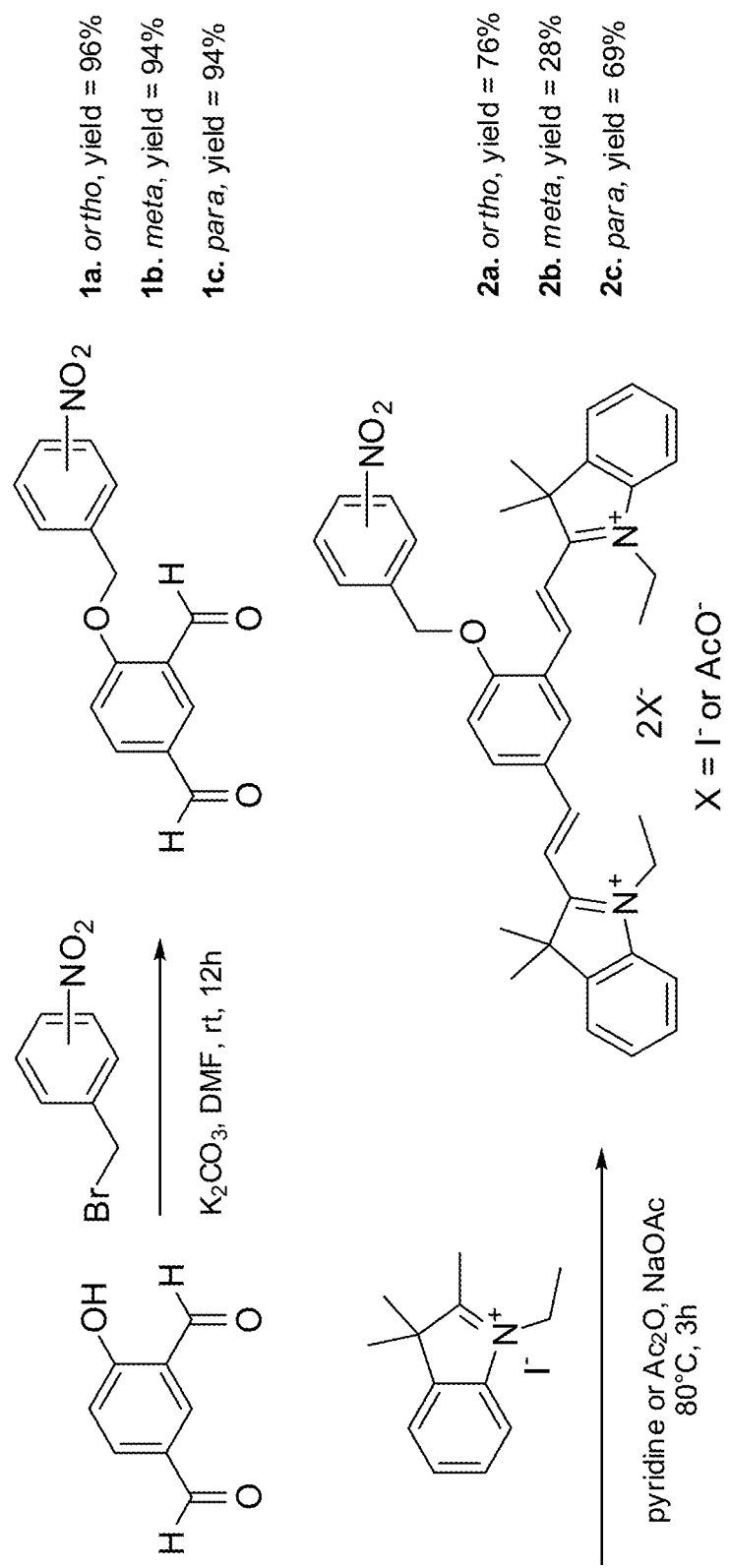
FIG. 10 illustrates exemplary synthesis protocols for NTR activatable profluorescent probes 2a-c.

In an effort to detect a mitochondrial nitroreductase which could be used for mitochondrial imaging, we designed a positively charged[6] fluorogenic probe which could potentially be triggered by a nitroreductase.[14] The QCy7 system[15] seemed to be a good candidate. It exhibits an emission wavelength in the NIR region which affords good cell imaging efficiency by diminishing the background and enhancing light penetrability. Also, the presence of indoles permitted the introduction of positive charge by simple indole alkylation (FIG. 10). The preparation of ortho, meta and para substituted 4-nitrobenzyloxy-isophthalaldehydes provided the alkylated precursors (1a-c) required for synthesis of the protected QCy7 dyes. The dialdehydes were used for preparation of three new probes by treatment with an excess of 1-ethyl-2,3,3-trimethyl-3H-indolium iodide (pyridine, 80° C., 3 h) as outlined in FIG. 10.

Figure 6A:
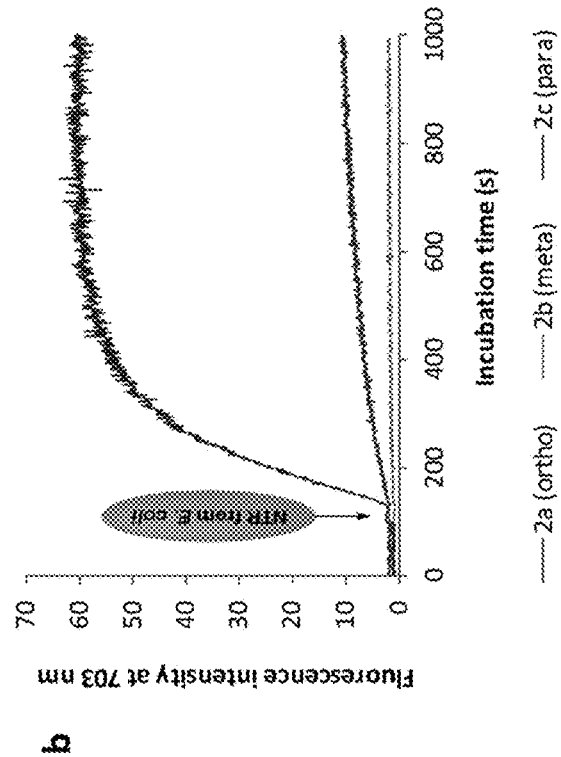
FIGS. 6A-6D. (a) Selective activation of 2c in vitro by $E.$ $coli$ nitroreductase. (b) Time dependent fluorescence emission by 2a, 2b and 2c (excitation at 572 nm; emission at 703 nm) in PBS at 25° C. following treatment with $E.$ $coli$ NTR (1 µg mL$^{-1}$) and 0.5 mM NADH. (c) Absorbance spectrum evolution with time during incubation of probe 2c in 25 µM PBS buffer, pH 7.4, with $E.$ $coli$ NTR (1 µg mL$^{-1}$) and 0.5 mM NADH. (d) Development of fluorescence from 10 µM 2c following treatment with 1 µg mL$^{-1}$ DT diaphorase (DTD) or nitroreductase (NTR) in 10 mM PBS buffer, pH 7.4, for 20 min at 25° C. with or without 50 mM NADH.
Figure 6B:
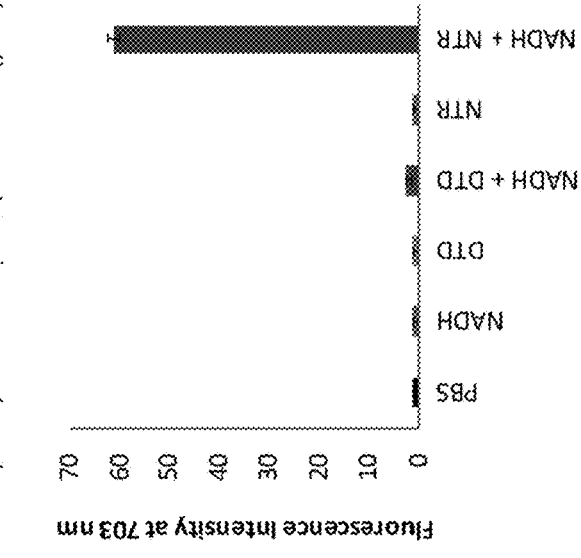
Figure 6C:
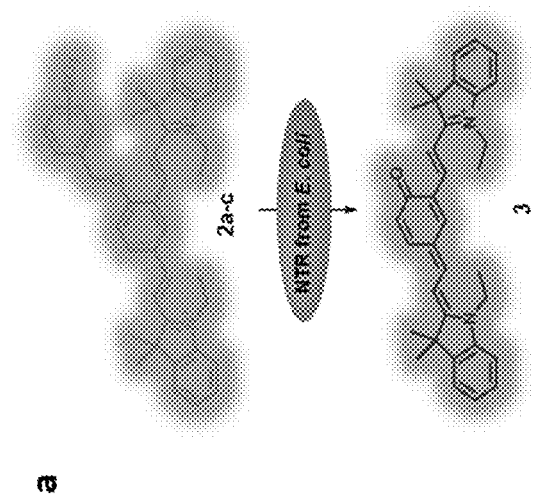
Figure 6D:
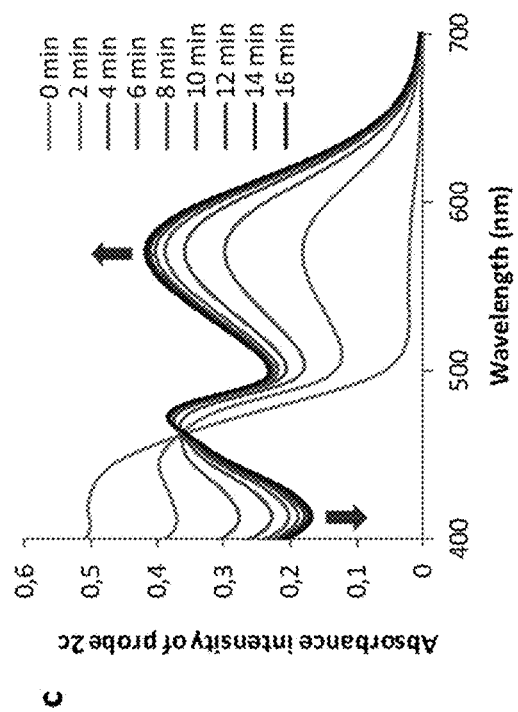
Figures 7A, 7B, 7C, 7D:
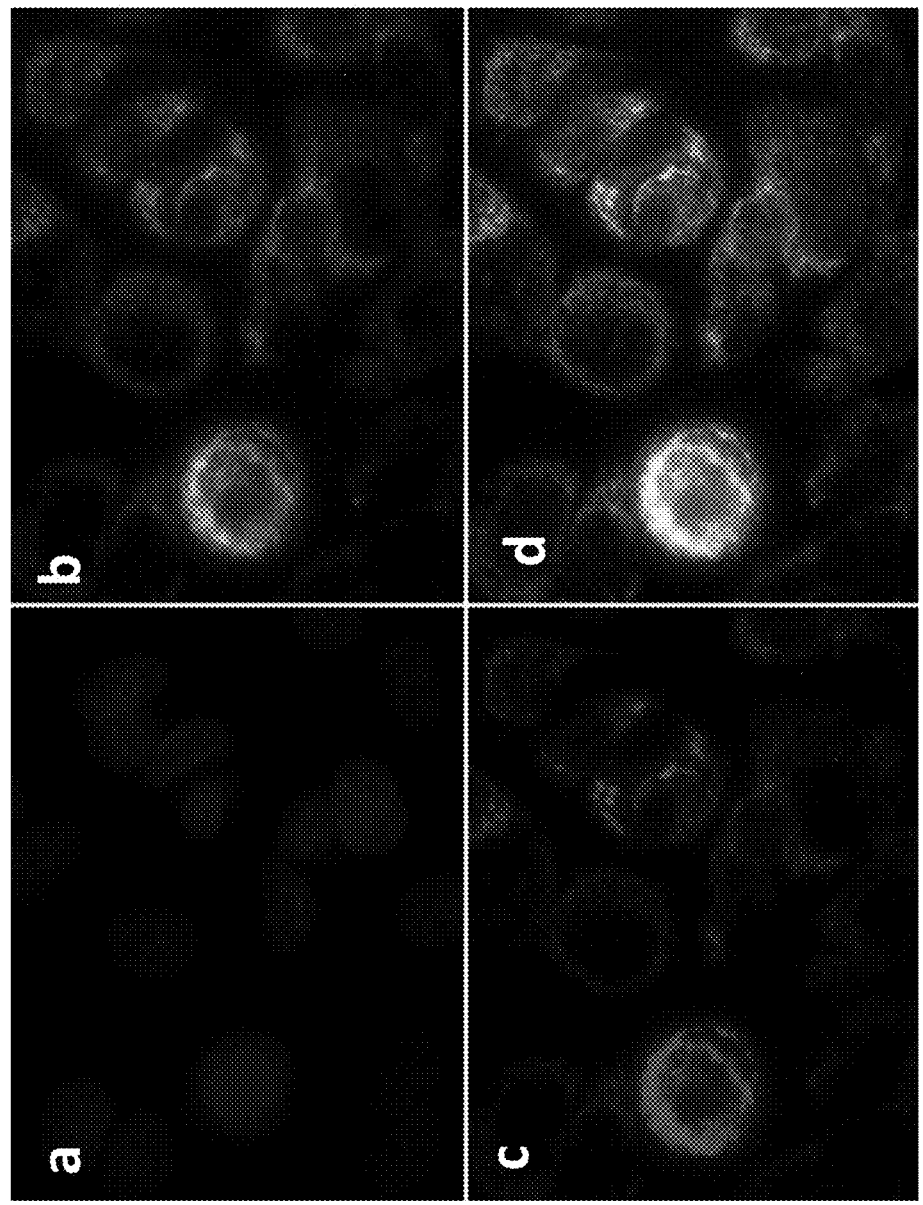
FIGS. 7A-7D demonstrate fluorescence emission from 2c colocalized to mitochondria in live A549 cells. Cells were stained with (a) 2.5 µg mL$^{-1}$ DAPI for nuclear staining, (b) 100 nM MitoTracker Green FM for mitochondrial staining, (c) 10 µM 2c for NTR detection, and (d) overlay of a, b and c.
Figure 11:
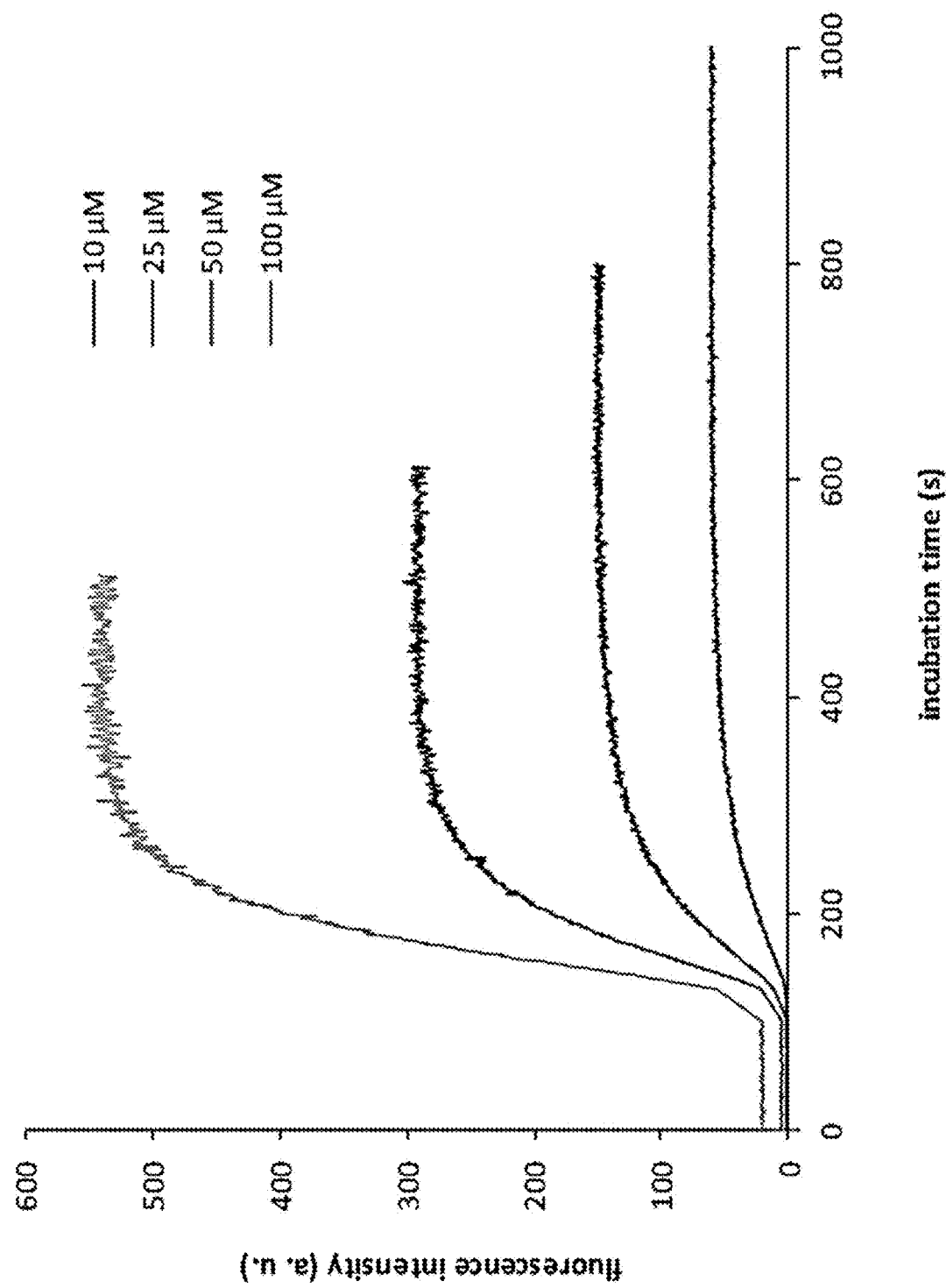
FIG. 11 is a fluorescence emission time course of 2c at different concentrations in PBS at 25° C. with NADH (0.5 mM) and $E.$ $coli$ nitroreductase (1 µg mL$^{-1}$). Excitation was carried out at 572 nm and the emission was monitored at 703 nm.
Figure 12:
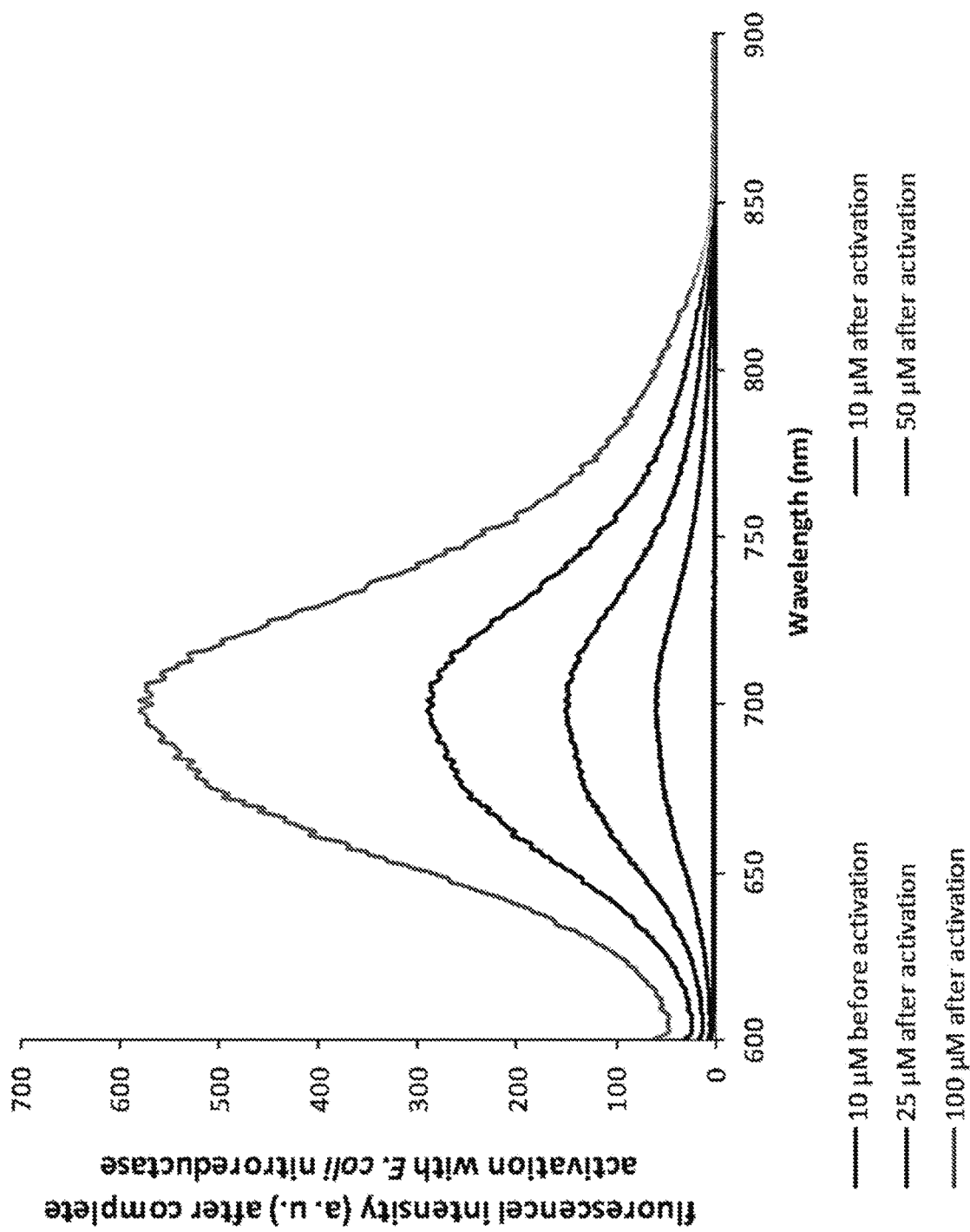
FIG. 12 is a fluorescence emission spectrum (excitation at 572 nm) after complete activation of 2c at different concentrations in PBS at 25° C. with 0.5 mM NADH and $E.$ $coli$ NTR (1 µg mL$^{-1}$). There was a linear correlation between fluorescence intensity and probe concentration.
Figure 12:
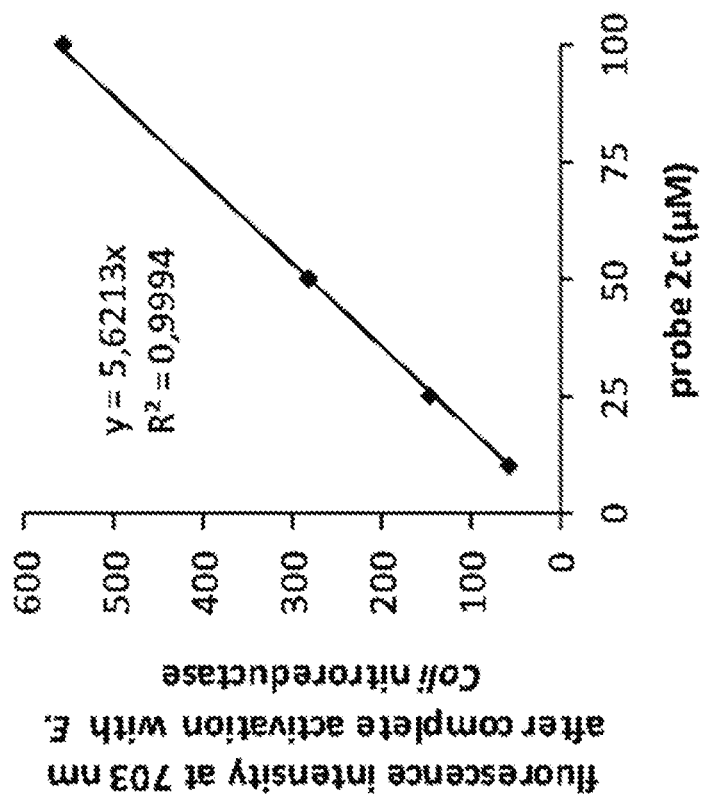
Figure 13:
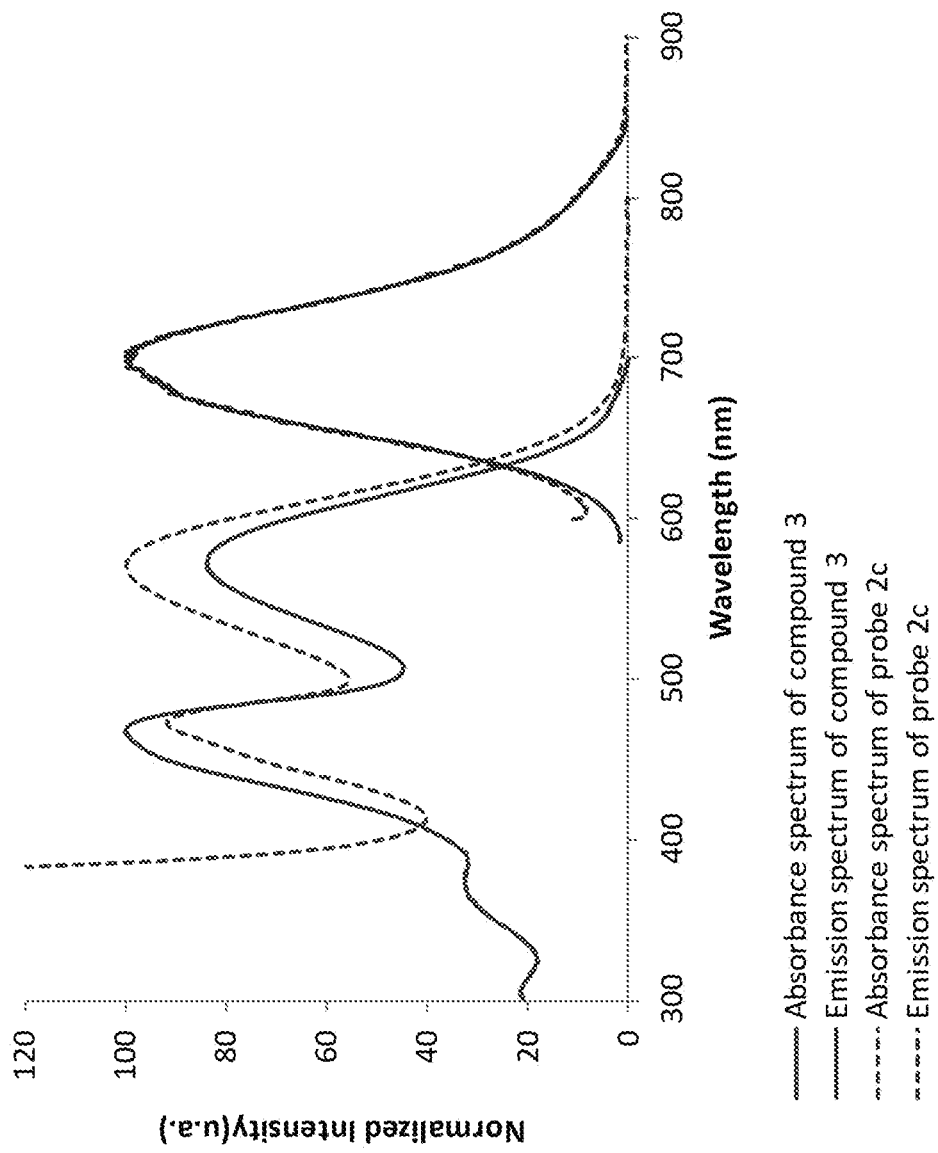
FIG. 13 is a comparison of absorbance and emission spectra recorded in phosphate buffered saline (PBS), pH 7.4, at 25° C. of compound 3 and probe 2c, after the later was activated with $E.$ $coli$ nitroreductase.
Figures 14A, 14B, 14C, 14D:
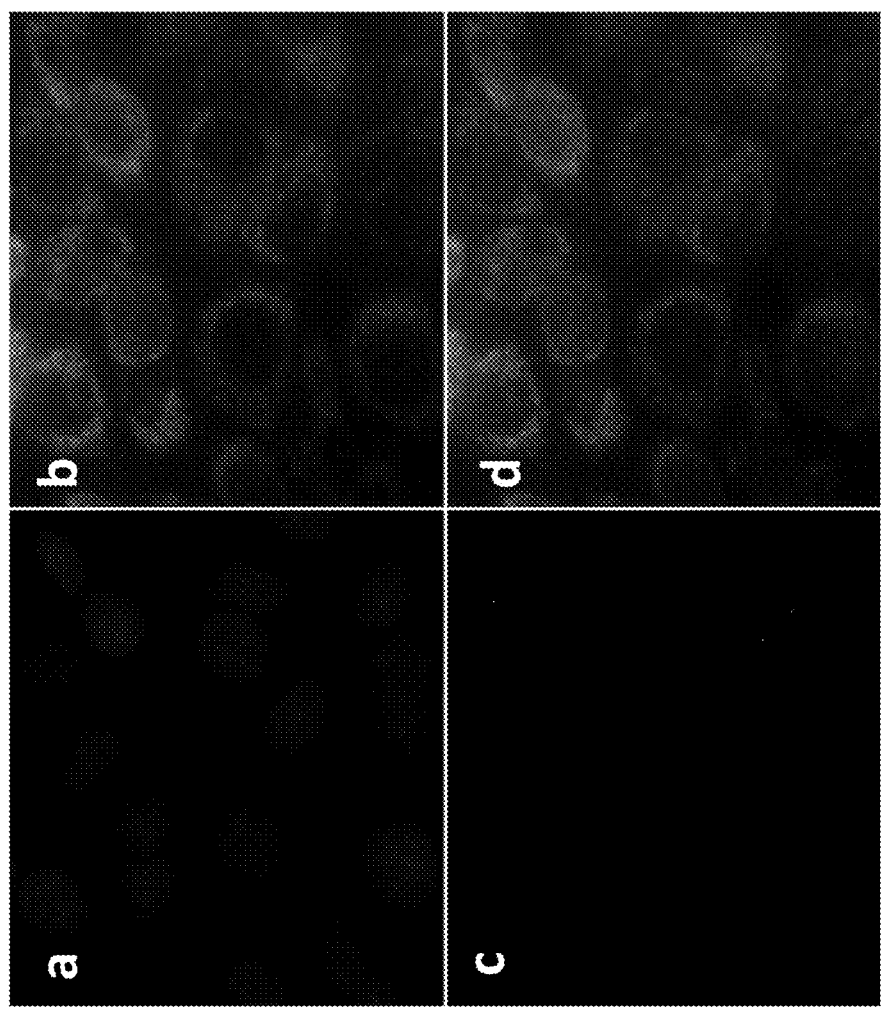
FIGS. 14A-14D present images of unactivated 2a in live A549 cells. Live cells were stained with (a) 2.5 µg mL$^{-1}$ DAPI for nucleus staining, (b) 100 nM MitoTracker Green FM for mitochondria staining, (c) 10 µM 2a for NTR detection and (d) overlay of panels a, b, and c.
Figures 15A, 15B, 15C, 15D:
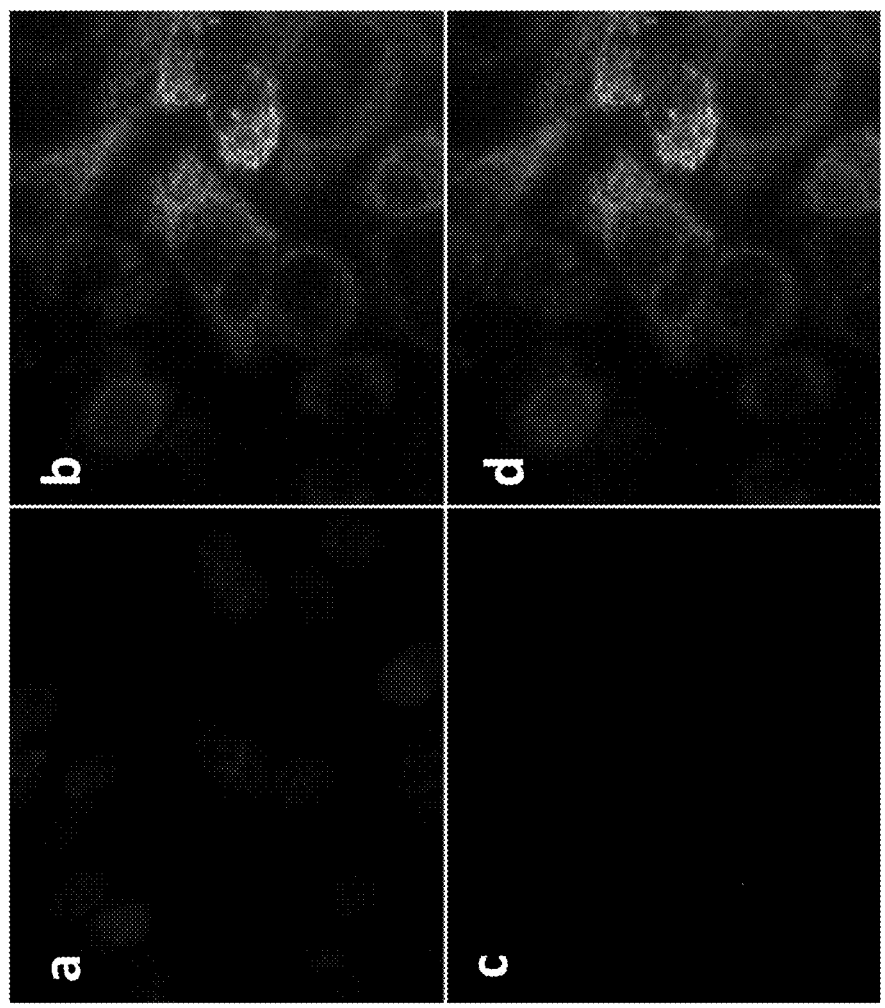
FIGS. 15A-15D present images of unactivated live A549 cells. Live cells were stained with (a) 2.5 µg mL$^{-1}$ DAPI for nucleus staining, (b) 100 nM MitoTracker Green FM for mitochondria staining, (c) 10 µM 2b for NTR detection and (d) overlay of panels a, b, and c.

The strategy for the release of the fluorescent NIR dye from a non-fluorescent precursor via mitochondrial nitroreductase-mediated reduction involved successive reduction, then elimination (FIG. 5b). The use of ortho, meta and para substituted probes (2a-2c) was crucial because it enabled the investigation of the proposed transformation in greater detail. Even if the reductive elimination of the ortho and para substituted probes proved to be practicable, none should occur in the case of meta analogue 2b. To assess the viability of these probes for the detection of nitroreductase activity, we first validated the probes in a cell free system using purified E. coli nitroreductase. Probes 2a-c (10 µM) were incubated in PBS buffer, pH 7.4, containing 0.5 mM NADH. After a short time, during which no fluorescence was observed, the nitroreductase was added (1 µg mL$^{-1}$) and the development of fluorescence was monitored as a function of time (FIGS. 6b, 6c). As expected, no fluorescence increase was observed for the probe 2b (meta substituted).[16] Conversely, good activation was observed for 2a and 2c, which are ortho and para-substituted, respectively. This confirmed what we expected, but also revealed that the activation of 2c was much faster than the activation of 2a, and increased with increasing substrate concentration (FIGS. 11 and 12). This can be explained by a better binding of the para-nitrobenzyl compounds in the nitroreductase enzyme active site as reported recently by Li et al.[10] The selectivity of the probe was also investigated using DT diaphorase, another two-electron reductase capable of activating small molecules.[17] As shown in FIG. 6d, significant activation occurred only in the presence of the nitroreductase+NADH. The monitoring of the absorbance spectrum during the NTR activation of 2c showed an increase of the absorbance band centered at 572 nm. This confirms that the released fluorescent dye is effectively of the QCy7 type by comparison with an authentic standard prepared by chemical synthesis (FIG. 13). With the viability of this probe thus confirmed, we carried out microscopy experiments employing A549 cancer cells. The incubation of 10 µM 2c with the cells for 4 hours was followed by the addition of 100 nm mitotracker green (40-minute incubation). The results clearly show the appearance of a red signal (FIG. 7c) characteristic of the release of QCy7 dye 3. The green channel (FIG. 7b) illustrates visualization of the mitochondria by mitotracker green. Superposition of panels a-c (FIG. 7d) shows complete overlap of the red and green signals, resulting in a yellow signal around the nucleus (stained in blue using DAPI).[18] As a control, probes 2a and 2b have also been tested, and neither provided a good signal (FIGS. 14 and 15). For 2b this is understandable as no elimination process is possible, as confirmed during the in vitro tests. In the case of 2a, we assume that the low kinetics of the reduction (c.f. FIG. 6b) is probably the cause of the absence of a strong signal. The appearance of a signal from 2c was also concentration dependent (FIG.

16). This constitutes the first direct visualization of nitroreductase activity localized in mitochondria. Notably, no hypoxic condition was required, i.e. the observed activity must be of type I, but this does not exclude the possible additional presence of type II nitoreductases in the mitochondria.

Figure 8A:
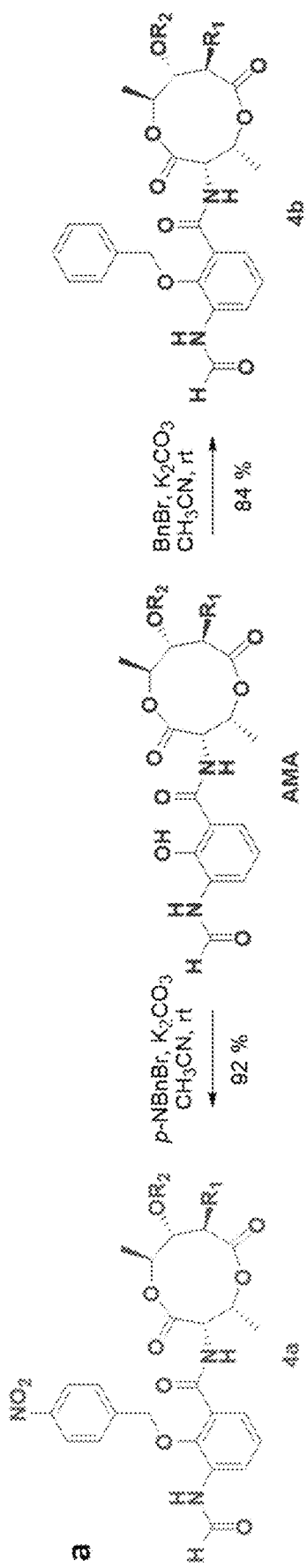
FIGS. 8A-8C demonstrate use of NTR for antimycin A (AMA) release in mitochondria. (a) Syntheses of p-nitrobenzyl-O-AMA (4a) and benzyl-O-AMA (4b) through alkylation of AMA. (b) Time course of appearance of AMA fluorescence ($\lambda_{em}$~425 nm)[20] during microscopy experiments in live A549 cancer cells treated with AMA and its alkylated derivatives 4a and 4b at 25 µM concentrations. The need for high concentrations of 4a/4b reflected the low quantum yield of the released AMA (~0.06). (c) AMA fluorescence signal after release by nitroreductase from alkylated analogues of AMA. Free AMA appeared exclusively in the mitochondria following treatment with compound 4a, while treatment with 4b resulted in no significant release of AMA.
Figure 8B:
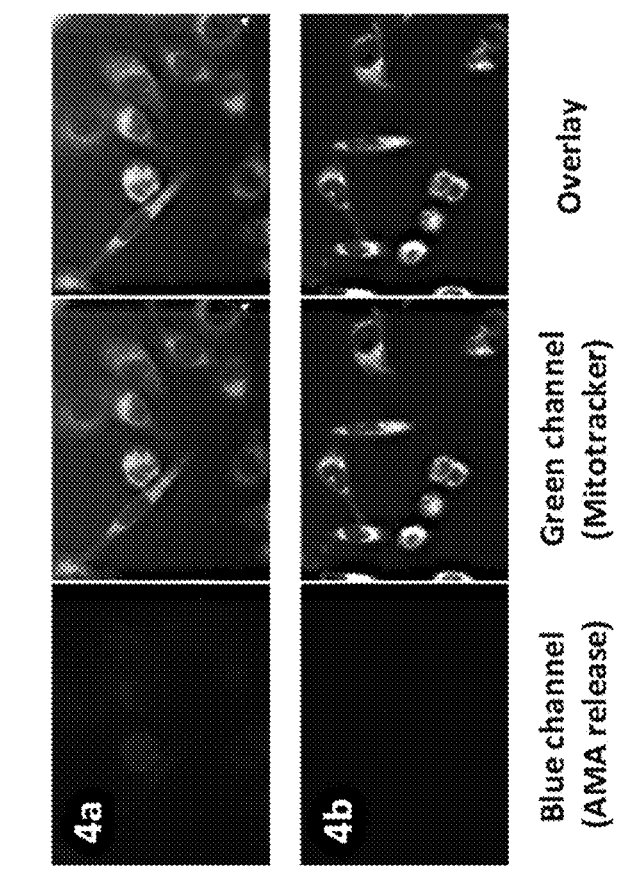
Figure 8C:
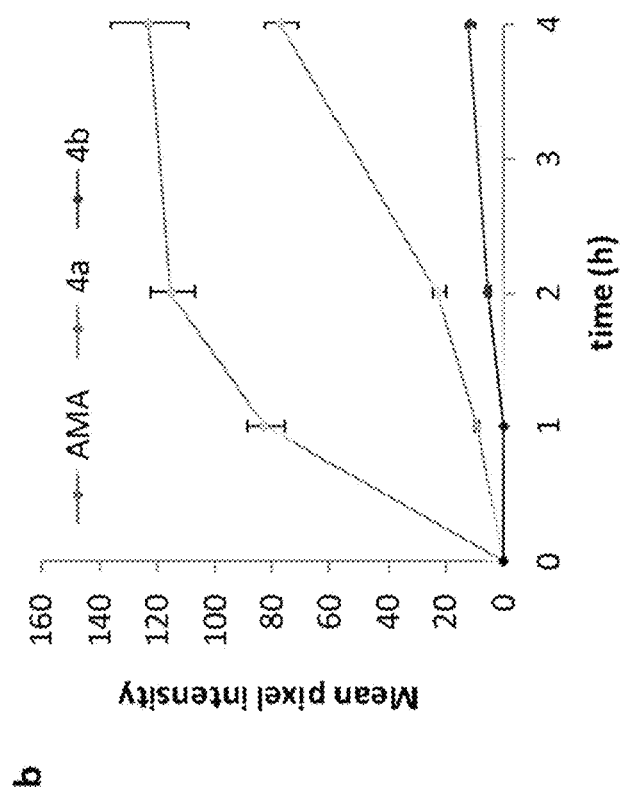
Figure 17:
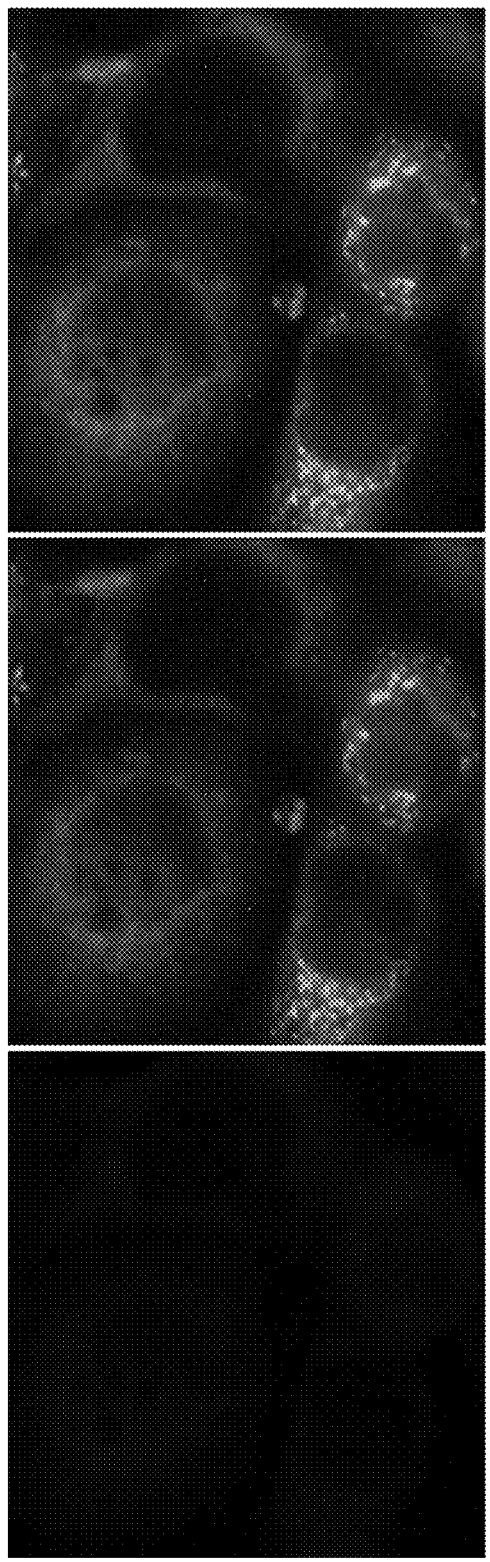
FIG. 17 is a comparison of the spatial distributions of mitochondria and AMA in A549 cells treated with AMA.

The finding of nitroreductase activity associated with the mitochondria of human cells encouraged us to design a new prodrug based on the mitochondrial poison antimycin A (AMA). It has recently been noted that AMA is toxic only at relatively high concentration,[19] plausibly due to a lack of facile access to the mitochondria. Further, it has been shown that there is at least one locus of action for AMA which does not involve the respiratory chain.[20] By O-alkylating AMA with a p-nitrobenzyl moiety, it seemed possible that we might facilitate mitochondrial delivery and release the active form of the compound only in the mitochondria. Accordingly, 0-p-nitrobenzyl-AMA (4a) was prepared in good yield by alkylation of AMA (FIG. 8a). Also prepared as a control was O-benzyl-AMA (4b). Compounds 4a and 4b lack fluorescence while AMA is fluorescent.[20] In comparison, A549 cells treated with AMA resulted in a distribution of AMA which did not fully colocalize with mitochondria (FIG. 17). Accordingly, it is possible to monitor the release of AMA within the mitochondria after enzymatic reduction of the nitro moiety in 4a. As anticipated, AMA was released from 4a by the action of mitochondrial nitroreductase, but not to a significant extent from 4b (FIG. 8b) and its appearance was localized to the mitochondria (FIG. 8c).[21]

Figures 9A, 9B:
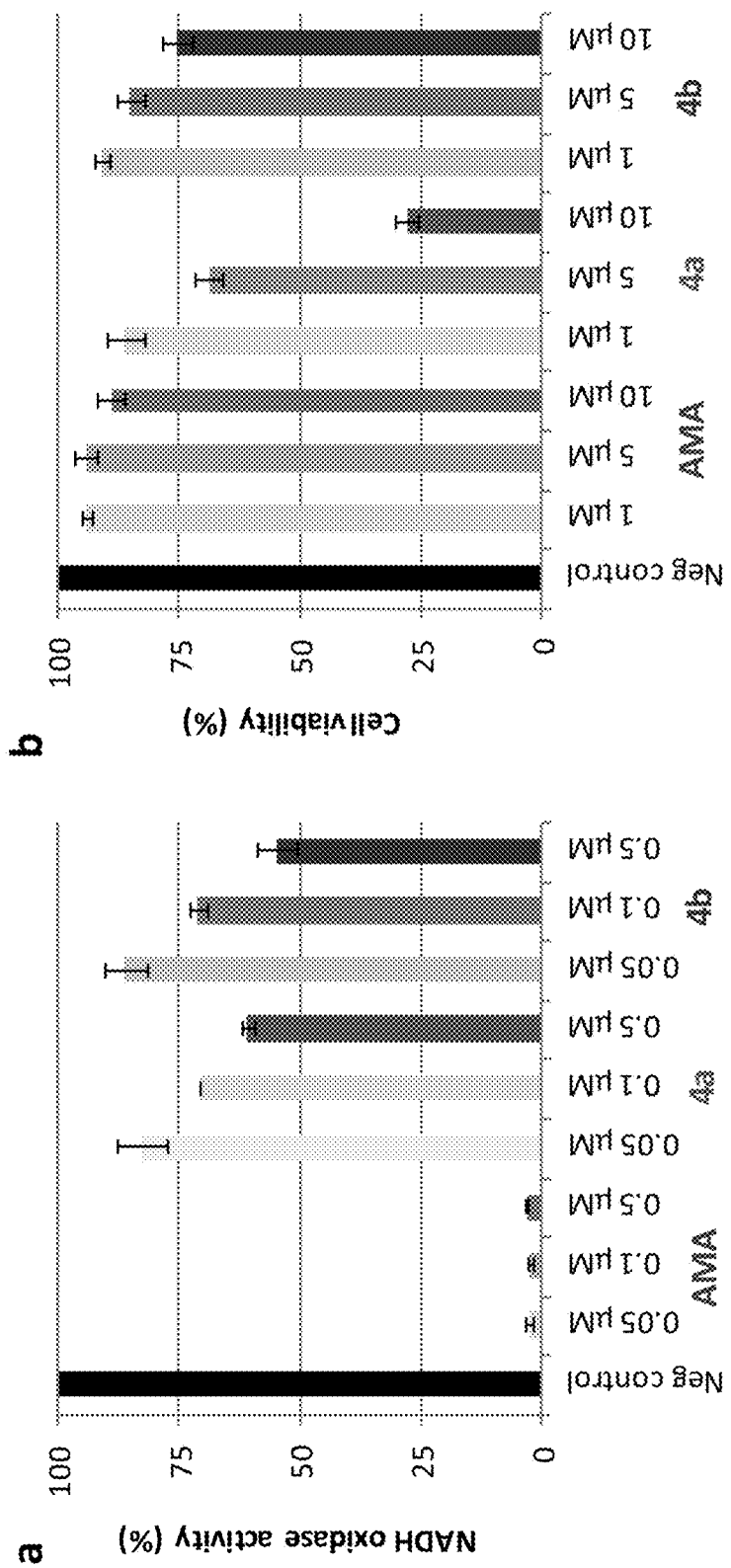
FIGS. 9A-9B present biological activity of AMA, 4a and 4b (a) NADH oxidase activity assays on AMA, 4a and 4b at 0.05, 0.1 and 0.5 µM concentrations. (b) Toxicity of AMA 4a and 4b toward A549 lung cancer cells after 24 h of incubation at 1, 5 and 10 µM concentrations.

The evaluation of 4a and 4b in comparison with AMA was carried out by comparing their effects both on the activity of the mitochondrial respiratory chain and on cell viability. As shown in FIG. 9a, AMA was a potent inhibitor of NADH oxidase, which measures the activity of mitochondrial respiratory complexes I, III, and IV. While AMA inhibited NADH oxidase essentially completely at 50 nM concentration, 4a and 4b exhibited comparable, and much weaker activity. This is not surprising given the putative importance of the phenolic moiety in AMA in association with the respiratory chain through hydrogen bonding.[22] In spite of their similar inhibitory activity toward NADH oxidase, 4a was found to be much more cytoxic toward A549 cancer cells than 4b, no doubt due to the conversion of 4a to AMA within the mitochondria by the nitroreductase (FIG. 9b). Compound 4a was considerably more cytotoxic than exogenously added AMA, underscoring the belief that the latter is not delivered efficiently to the mitochondria. This represents the first example of the use of a mitochondrial nitroreductase for selective mitochondrial drug delivery, and should be extensible to numerous other classes of potential therapeutic agents.

In summary, this example demonstrates the identification of a mitochondrial type I nitroreductase activity and the design and preparation of a caged (non-fluorescent) probe. Our data demonstrates that the caged probe is converted to a fluorescent compound by the nitroreductase when it enters cell mitochondria. By preparing a novel prodrug of the mitochondrial poison antimycin A, it is possible to facilitate the delivery of antimycin to cell mitochondria, where it is unmasked by the mitochondrial nitroreductase and exhibits increased cytotoxicity relative to antimycin A administered alone. This provides the first example of an enzymatically activated mitochondrial probe. Further, we demonstrated that this enzymatic activity can be exploited both for the selective NIR imaging of mitochondria, and for mitochondrial targeting by the activation of a mitochondrial poison specifically within that organelle. These findings represent the first use of a mitochondrial enzyme activity for unmasking agents for mitochondrial fluorescent imaging and therapy, and may prove to be more broadly applicable for imaging mitochondria, and for selective delivery of the active form of therapeutic agents designed to work within the mitochondria of diseased cells.

Methods and Materials for Example 1

All experiments requiring anhydrous conditions were conducted in flame-dried glassware fitted with a rubber septum under a positive pressure of dry argon. Reactions were performed at room temperature unless otherwise indicated. Analytical thin layer chromatography was performed using glass plates pre-coated with silica gel (0.25 mm, 60 Å pore size, 230-400 mesh, Silicycle) impregnated with a fluorescent indicator (254 nm). TLC plates were visualized by exposure to ultraviolet light (UV) or by staining using 12. Flash column chromatography was performed employing silica gel (60 Å pore size, 40-63 μm, standard grade, Silicycle). Fluorescence quantum yields were measured at 25° C. by a relative method using cresyl violet (CV, $\Phi_F$=56% in EtOH) as a standard.[1] The following equation was used to determine the relative fluorescence quantum yield:

$$\Phi_F(x)=(A_S/A_X)(F_X/F_S)(n_X/n_S)^2\Phi_F(s)$$

where A is the absorbance (in the range of 0.01-0.1 A.U.), F is the area under the emission curve, n is the refractive index of the solvents (at 25° C.) used in measurements, and the subscripts s and x represent standard and unknown, respectively. The following refractive index values were used: 1.362 for EtOH and 1.337 for PBS.

General Procedure for the Preparation of Nitrobenzylated 4-Hydroxyisophthalaldehydes.

A solution containing 50.0 mg (0.33 mmol) of 4-hydroxyisophthalaldehyde and 91.2 mg (0.66 mmol) of $K_2CO_3$ in 2 mL of dry DMF was stirred under argon at room temperature for 10 min. The, 85.5 mg (0.40 mmol) of nitrobenzyl bromide was added and the reaction mixture was stirred under argon overnight. After the reaction was completed (monitored by silica gel TLC using 2:1 hexanes-ethyl acetate), the reaction mixture was diluted with 50 mL of EtOAc and then washed with two 50-mL portions of brine and with 50 mL of water. The organic layer was dried ($MgSO_4$) and concentrated under diminished pressure. The crude mixture was solubilized in the minimum amount of $CH_2Cl_2$ and hexane was added to effect the precipitation of a colorless solid. The precipitate was isolated by filtration to give the desired compounds 1.

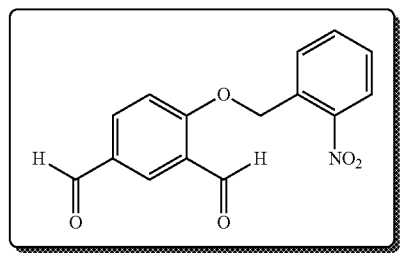

4-(o-Nitrobenzyloxy)isophthalaldehyde (1a).

The compound was prepared using 85.5 mg (0.40 mmol) of o-nitrobenzyl bromide. Compound 1a was obtained as a colorless solid: yield 90.0 mg (96%); mp 145° C.; silica gel TLC $R_f$ 0.60 (1:1 hexanes-ethyl acetate); $^1$H NMR (CDCl$_3$) δ 5.73 (s, 2H), 7.24 (d, 1H, J=8.7 Hz), 7.58 (t, 1H, J=8.1 Hz), 7.77 (t, 1H, J=7.5 Hz), 7.92 (t, 1H, J=7.8 Hz), 8.14 (m, 1H), 8.24 (d, 1H, J=8.2 Hz), 8.39 (m, 1H), 9.97 (d, 1H, J=0.7 Hz) and 10.58 (d, 1H, J=1.1 Hz); $^{13}$C NMR (CDCl$_3$) δ 68.1, 113.7, 125.4, 125.5, 128.5, 129.3, 130.5, 131.8, 132.7, 134.6, 136.2, 147.0, 164.1, 188.2 and 190.0; mass spectrum (APCI), m/z 286.0711 (M+H)$^+$ ($C_{15}H_{12}N_2O_5$ requires m/z 286.0715).

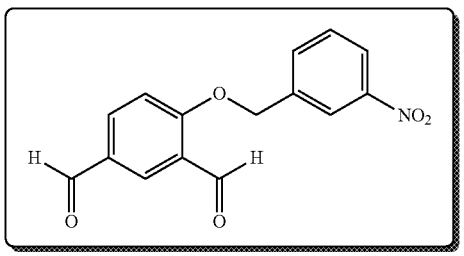

4-(m-Nitrobenzyloxy)isophthalaldehyde (1b).

The compound was prepared using 85.5 mg (0.40 mmol) of m-nitrobenzyl bromide. Compound 1b was obtained as a colorless solid: yield 88.3 mg (94%); mp 158° C.; silica gel TLC $R_f$ 0.45 (1:1 hexanes-ethyl acetate); $^1$H NMR (CDCl$_3$) δ 5.40 (s, 2H), 7.20 (d, 1H, J=8.7 Hz), 7.65 (dt, 1H, J=8.3 and 1.4 Hz), 7.83 (d, 1H, J=7.1 Hz), 8.14 (dt, 1H, J=8.6 and 1.8 Hz), 8.26 (d, 1H, J=8.2 Hz), 8.34 (s, 1H), 8.38 (t, 1H, J=1.8 Hz), 9.97 (d, 1H, J=1.4 Hz) and 10.55 (d, 1H, J=1.8 Hz); $^{13}$C NMR (CDCl$_3$) δ 69.8, 113.4, 122.4, 123.8, 125.4, 130.3, 130.5, 132.4, 133.3, 135.9, 137.2, 148.5, 164.2, 188.1 and 190.1; mass spectrum (APCI), m/z 286.0718 (M+H)$^+$ (C$_{15}$H$_{12}$N$_2$O$_5$ requires m/z 286.0715).

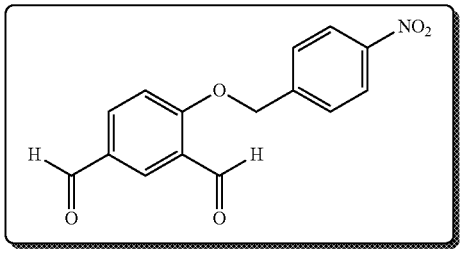

4-(p-Nitrobenzyloxy)isophthalaldehyde (1c).

The compound was prepared using 85.5 mg (0.40 mmol) of p-nitrobenzyl bromide. Compound 1c was obtained as a colorless solid: yield 88.5 mg (94%); mp 185° C.; silica gel TLC $R_f$ 0.45 (1:1 hexanes-ethyl acetate); $^1$H NMR (CDCl$_3$) δ 5.41 (s, 2H), 7.17 (d, 1H, J=8.7 Hz), 7.65 (d, 2H, J=8.8 Hz), 8.12 (dd, 1H, J=8.7 and 2.2 Hz), 8.30 (d, 2H, J=8.8 Hz), 8.38 (d, 1H, J=2.2 Hz), 9.97 (s, 1H) and 10.56 (s, 1H); $^{13}$C NMR (CDCl$_3$) δ 69.8, 113.4, 124.3, 125.4, 127.9, 130.5, 132.5, 135.9, 142.2, 148.2, 164.1, 188.1 and 190.0; mass spectrum (APCI), m/z 286.0714 (M+H)$^+$ (C$_{15}$H$_{12}$N$_2$O$_5$ requires m/z 286.0715).

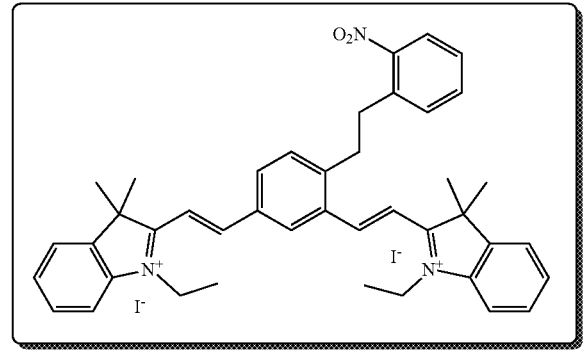

4-(o-Nitrobenzyloxy)-QCy7 probe (2a).

To a mixture of 20 mg (0.07 mmol) of 4-(o-nitrobenzyloxy)-isophthalaldehyde, 48.5 mg (0.15 mmol) of 1-ethyl-2,3,3-trimethyl-3H-indolium iodide and 12.6 mg (0.15 mmol) of sodium acetate in 1 mL of dry acetic anhydride was applied a positive pressure of argon. The reaction mixture was stirred at 80° C. for 45 minutes (min) under argon, leading to the precipitation of the desired dye as an orange solid. The solvent was removed by centrifugation and the resulting solid was washed twice with acetic anhydride then twice with Et$_2$O. The solid was dried under vacuum to furnish 2a as an orange solid: yield 47 mg (76%); mp 178-180° C.; silica gel TLC $R_f$ 0.30 (95:5 CH$_2$Cl$_2$-MeOH); $^1$H NMR (CDCl$_3$) δ 1.65 (m, 6H), 1.80 (s, 6H), 2.06 (s, 6H), 5.11 (q, 2H, J=7.2 Hz), 5.18 (q, 2H, J=7.2 Hz), 5.79 (s, 2H), 7.43 (d, 1H, J=9.0 Hz), 7.50-7.65 (m, 9H), 7.75 (m, 2H), 8.03-8.13 (m, 2H), 8.29 (d, 1H, J=16.4 Hz), 8.64 (d, 1H, J=16.4 Hz), 9.04 (d, 1H, J=16.1 Hz), 9.36 (d, 1H, J=8.8 Hz) and 9.90 (s, 1H); $^{13}$C NMR (CDCl$_3$) δ14.8, 14.9, 21.2, 27.2, 44.3, 44.7, 52.7, 53.2, 69.0, 112.1, 113.9, 114.2, 114.3, 114.6, 123.1, 123.2, 123.6, 125.5, 129.1, 129.4, 129.9, 130.3, 130.4, 131.0, 134.2, 136.0, 139.6, 140.3, 144.0, 144.7, 148.2, 148.5, 155.0, 161.8, 182.3 and 182.8; mass spectrum (APCI), m/z 624.3210 (M−H)$^+$ (C$_{41}$H$_{42}$N$_3$O$_3$ requires m/z 624.3226).

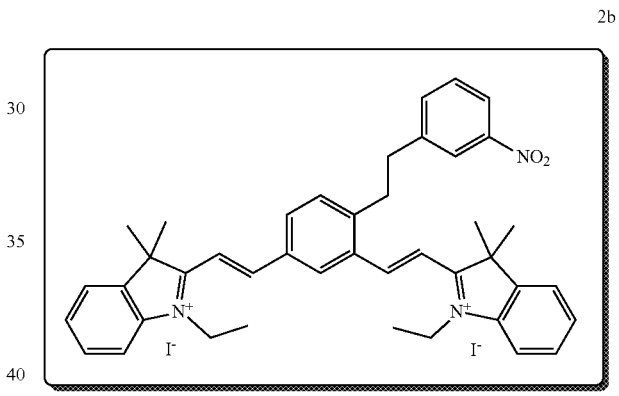

4-(m-Nitrobenzyloxy)-QCy7 probe (2b).

To a mixture of 20 mg (0.07 mmol) of 4-(m-nitrobenzyloxy)-isophthalaldehyde and 48.5 mg (0.15 mmol) of 1-ethyl-2,3,3-trimethyl-3H-indolium iodide in 1 mL of dry pyridine was applied a positive pressure of argon. The reaction mixture was stirred at 80° C. for 5 hours (h) under argon. The cooled reaction mixture was centrifuged to remove the solid residue. The supernatant was diluted in 1 mL of CH$_2$Cl$_2$ and added dropwise to 20 mL of diethyl ether to induce the precipitation of the desired compound. The resulting solid was isolated by filtration, washed with Et$_2$O, dissolved in a minimum amount of CH$_2$Cl$_2$ and applied to a 1000μ preparative silica gel TLC plate (20×10 cm) for purification. Elution with 97:3 CH$_2$Cl$_2$-MeOH afforded compound 2b as an orange solid: yield 17 mg (28%); mp 183-185° C.; silica gel TLC $R_f$ 0.30 (95:5 CH$_2$Cl$_2$-MeOH); $^1$H NMR (CDCl$_3$) δ (1.67 m, 6H), 1.83 (s, 6H), 2.09 (s, 6H), 5.12 (q, 2H, J=7.3 Hz), 5.23 (q, 2H, J=7.3 Hz), 5.52 (s, 2H), 7.52 (m, 1H), 7.54-7.60 (m, 5H), 7.60-7.64 (m, 3H), 7.69 (t, 1H, J=8.1 Hz), 7.86 (d, 1H, J=7.7 Hz), 8.09 (d, 1H, J=16.2 Hz), 8.30 (d, 1H, J=8.1 Hz), 8.39 (d, 1H, J=16.2 Hz), 8.51 (m, 1H), 8.83 (d, 1H, J=16.2 Hz); 9.15 (d, 1H, J=16.3 Hz), 9.59 (dd, 1H, J=9.1 and 1.9 Hz) and 10.01 (d, 1H, J=1.9 Hz); $^{13}$C NMR (CDCl$_3$) δ14.9, 15.1, 27.2, 27.4, 44.2, 44.9, 52.7, 53.3, 70.2, 112.1, 113.6, 114.1, 114.4, 114.6, 121.4, 123.2, 123.7, 129.3, 129.5, 129.9, 130.3, 133.6, 136.1, 137.9, 140.0, 140.3, 143.9, 144.8, 148.2, 148.7, 155.1, 161.8, 182.1 and 182.9; mass spectrum (APCI), m/z 624.3212 (M−H)⁺ (C₄₁H₄₂N₃O₃ requires m/z 624.3226).

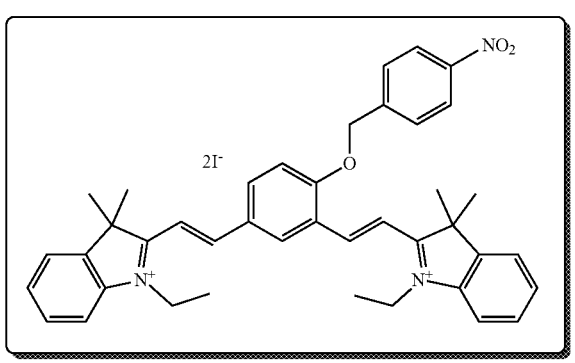

4-(m-Nitrobenzyloxy)-QCy7 probe (2c).

To a mixture 20 mg (0.07 mmol) of 4-(p-nitrobenzyloxy)-isophthalaldehyde and 48.5 mg (0.15 mmol) of 1-ethyl-2,3,3-trimethyl-3H-indolium iodide in 1 mL of dry pyridine was applied a positive pressure of argon. The resulting reaction mixture was stirred at 80° C. for 3 h under argon leading to the precipitation of the desired dye as an orange solid. The solvent was removed by centrifugation and the resulting solid was washed twice with cold pyridine then twice with Et₂O. The solid was then dried under vacuum to furnish compound 2b as an orange solid: yield 42.5 mg (65%); mp 203-205° C.; silica gel TLC R$_f$ 0.30 (95:5 CH₂Cl₂-MeOH); ¹H NMR (CDCl₃) δ 1.66 (m, 6H), 1.77 (s, 6H), 2.07 (s, 6H), 5.12 (q, 2H, J=7.2 Hz), 5.19 (q, 2H, J=7.2 Hz), 5.50 (s, 2H), 7.5-7.65 (m, 9H), 7.74 (d, 2H, J=8.6 Hz), 8.09 (d, 1H, J=16.3), 8.33 (d, 2H, J=8.6 Hz), 8.38 (d, 1H, J=16.4 Hz), 8.74 (d, 1H, J=16.4 Hz), 9.09 (d, 1H, J=16.2 Hz), 9.50 (dd, 1H, J=9.0 and 1.9 Hz) and 9.99 (d, 1H, J=1.9 Hz); ¹³C NMR (CDCl₃) δ14.9, 15.0, 27.2, 27.4, 44.3, 44.8, 52.5, 53.2, 70.6, 112.2, 113.7, 114.2, 114.3, 114.6, 123.1, 123.2, 124.2, 128.6, 129.2, 129.5, 129.9, 130.1, 130.4, 136.1, 140.1, 140.27, 140.29, 142.6, 143.7, 144.7, 148.2, 148.5, 155.0, 161.9, 182.0 and 182.8; HRMS (APCI), m/z 624.3220 (M−H)⁺ (C₄₁H₄₂N₃O₃ requires m/z 624.3226).

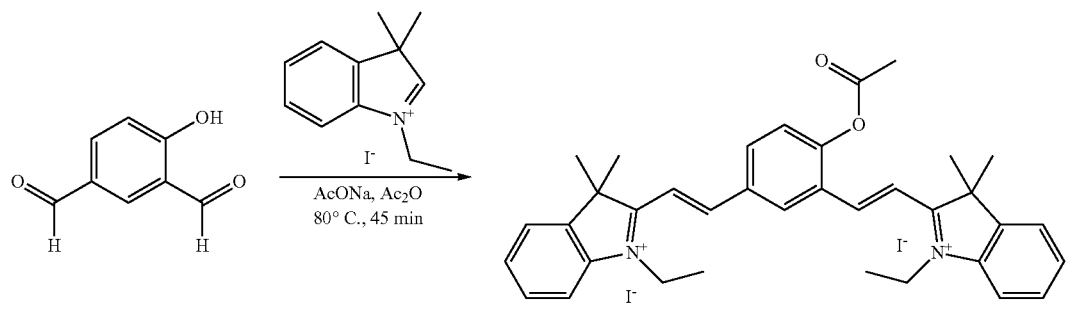

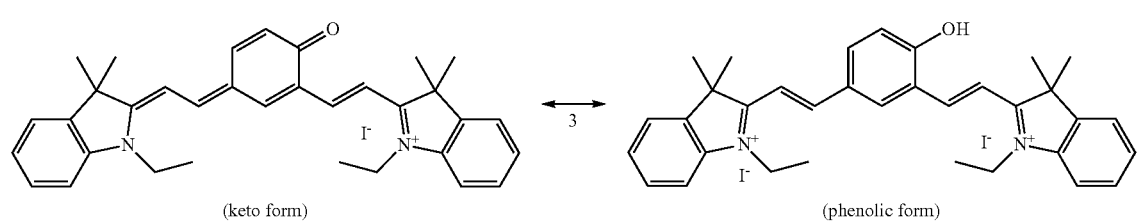

(keto form)      (phenolic form)

Acetyl-QCy7 (2d).

To a suspension containing 50.0 mg (0.33 mmol) of isophthalaldehyde, 218 mg (0.69 mmol) of 1-ethyl-2,3,3-trimethyl-3H-indolium iodide and 83.9 mg (1.02 mmol) of sodium acetate in 5 mL of dry acetic anhydride was applied a positive pressure of argon. The resulting reaction mixture was stirred at 80° C. for 45 min leading to the precipitation of the desired dye as an orange solid. The solvent was removed by centrifugation and the resulting solid was washed twice with acetic anhydride and with $Et_2O$. The solid was then dried under vacuum to afford 2c as an orange solid, which was used directly for the next step: yield 239 mg (92%); $^1$H NMR ($CDCl_3$) δ (1.70 m, 6H), 1.87 (s, 6H), 2.09 (s, 6H), 2.47 (s, 3H), 5.20 (q, 2H, J=7.4 Hz), 5.28 (q, 2H, J=7.4 Hz), 7.54-7.71 (m, 9H), 8.19 (d, 1H, J=16.1 Hz), 8.32 (d, 1H, J=16.2 Hz), 8.44 (d, 1H, J=16.2 Hz), 9.07 (d, 1H, J=16.3 Hz), 9.29 (d, 1H, J=8.7 Hz) and 10.00 (s, 1H); $^{13}$C NMR ($CDCl_3$) δ15.0, 15.2, 21.4, 27.0, 27.3, 44.8, 45.4, 52.9, 53.5, 114.2, 114.6, 115.1, 115.5, 123.2, 123.3, 124.4, 126.8, 129.6, 130.1, 130.3, 130.8, 133.3, 134.6, 137.6, 140.2, 140.3, 143.8, 144.9, 147.0, 153.8, 154.1, 167.9, 182.0 and 183.0; mass spectrum (MALDI), m/z 266.46 $(M)^{2+}/2$ (theoretical m/z 266.15).

Diethyl QCy7 (3).

To a solution of 30.0 mg (38.1 μmol) of the crude solid 2d in 1 mL of MeOH was added 5.25 mg (38.1 μmol) of $K_2CO_3$ and the resulting green solution was stirred at room temperature for 4 h. The reaction mixture was then diluted with 2 mL of $CH_2Cl_2$ and filtered through cotton to remove inorganic material. The filtrate was then concentrated under diminished pressure the crude residue was dissolved in 3:1 $CH_2Cl_2$—AcOH and purified by flash chromatography on a silica gel column (15×1 cm). Elution with 95:2.5:2.5 $CHCl_3$-MeOH—AcOH afforded 3 as a yellow solid: yield 12 mg (51%); silica gel TLC $R_f$ 0.25 (95:2.5:2.5 $CHCl_3$-MeOH—AcOH); $^1$H NMR ($CDCl_3$) δ1.16 (m, 3H), 1.27 (s, 3H), 1.63 (t, 3H, J=7.1 Hz), 1.79 (s, 6H), 2.09 (s, 3H), 3.21 (m, 1H), 3.32 (m, 1H), 5.00-5.12 (m, 2H), 5.81 (d, 1H, J=10.2 Hz), 6.56 (d, 1H, J=7.7 Hz), 6.74 (d, 1H, J=8.4 Hz), 6.83 (t, 1H, J=7.3 Hz), 7.07 (d, 1H, J=7.3 Hz), 7.17 (t, 1H, J=7.7 Hz), 7.42 (t, 1H, J=7.2 Hz), 7.47-7.58 (m, 5H), 7.89 (d, 1H, J=16.2 Hz), 8.06 (d, 1H, J=16.2 Hz) and 9.03 (s, 1H); $^{13}$C NMR ($CDCl_3$) δ 14.3, 14.5, 26.3, 27.5, 28.2, 37.9, 44.1, 51.9, 52.8, 103.7, 106.6, 109.7, 114.1, 116.1, 119.1, 121.0, 121.8, 122.7, 126.4, 126.6, 127.8, 129.3, 129.4, 129.8, 130.1, 136.2, 136.4, 140.6, 143.1, 146.9, 155.7, 155.7, 166.8 and 180.6; HRMS (APCI), m/z 489.2920 $(M)^+$ ($C_{34}H_{37}N_2O$ requires m/z 489.2900). quantum yield 6.1% (PBS buffer, pH 7.4)

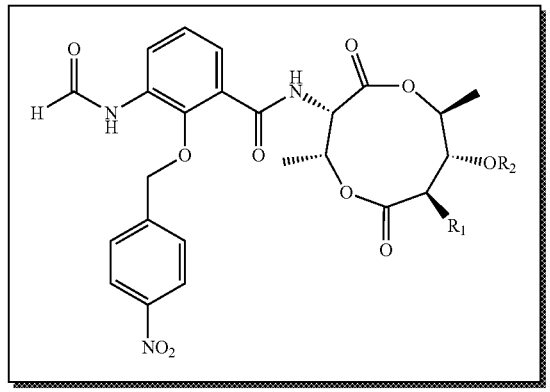

2-O-(p-Nitrobenzyl)AMA (4a).

A solution containing 10.0 mg (19.0 μmol) of antimycin A and 10.0 mg (76.0 μmol) of $K_2CO_3$ in 500 μL of dry $CH_3CN$ was stirred under argon. After 15 min, 7.00 mg (38.0 μmol) of p-nitrobenzyl bromide and a crystal of NaI were added. The reaction mixture was stirred at room temperature under argon for 12 h. The reaction was monitored by silica gel TLC (2:1 hexane-EtOAc) until it was complete. The crude reaction mixture was diluted with 1 mL of $CH_2Cl_2$ and filtered through cotton to remove inorganic material. The resulting solution was concentrated under diminished pressure and the residue was purified by preparative silica gel TLC plate (1000μ, 20×10 cm) Elution with 1:1 hexane-EtOAc afforded compound 4a as a colorless wax: yield 11 mg (84%); silica gel TLC $R_f$ 0.20 (1:1 hexanes-ethyl acetate); mass spectrum (APCI), $AMA_1$ m/z 684.3142 $(M+H)^+$ ($C_{35}H_{46}N_3O_{11}$ requires 684.3133); $AMA_2$ m/z 670.2965 $(M+H)^+$ ($C_{34}H_{44}N_3O_{11}$ requires 670.2976); $AMA_3$ m/z 656.2827 $(M+H)^+$ ($C_{33}H_{42}N_3O_{11}$ requires 656.2820); $AMA_4$ m/z 642.2659 $(M+H)^+$ ($C_{32}H_{40}N_3O_{11}$ requires 642.2663).

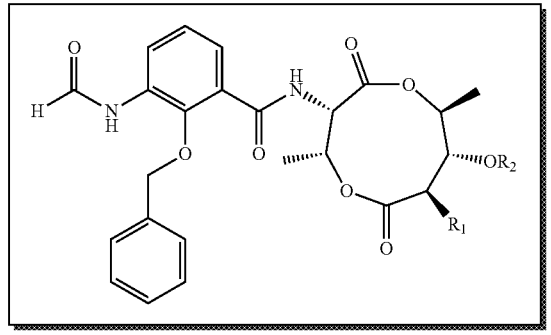

2-O-Benzyl-AMA (4b).

A solution containing 10.0 mg (19.0 μmol) of antimycin A and 10.0 mg (76.0 μmol) of $K_2CO_3$ in 500 μL of dry $CH_3CN$ was stirred under argon. After 15 min, 4.60 μL (38.0 μmol) of benzyl bromide and a crystal of NaI were added. The reaction mixture was stirred at room temperature under argon for 12 h. The reaction was monitored by silica gel TLC (2:1 hexane-EtOAc) until the reaction was complete. The crude reaction mixture was diluted with 1 mL of $CH_2Cl_2$ and filtered through cotton to remove inorganic material. The resulting solution was concentrated under diminished pressure and the residue was purified by preparative silica gel TLC plate (1000μ, 20×10 cm). Elution with 2:1 hexane-EtOAc afforded compound 4b as a colorless wax: yield 11.2 mg (92%); silica gel TLC $R_f$ 0.50 (1:1 hexanes-ethyl acetate); HRMS (APCI), $AMA_1$ m/z 639.3280 $(M+H)^+$ ($C_{34}H_{45}N_2O_9$ requires 639.3281); $AMA_2$ m/z 625.3141 $(M+H)^+$ ($C_{34}H_{45}N_2O_9$ requires 625.3125); $AMA_3$ m/z 611.2972 $(M+H)^+$ ($C_{33}H_{43}N_2O_9$ requires 611.2968); $AMA_4$ m/z 597.2813 $(M+H)^+$ ($C_{32}H_{41}N_2O_9$ requires 597.2812).

Fluorescence Monitoring.

A solution of fluorogenic probe was prepared in 1 mL of phosphate buffered saline (PBS) and 150 μL of the resulting solution was transferred into a quartz fluorescence cell. A volume of 1.51 μL of a 50 mM solution of NADH was then added to afford a final concentration of 0.5 mM and the resulting solution was incubated at 25° C. After excitation at 572 nm the emission of the released fluorophore was monitored at 703 nm over time with measurements recorded every 1 sec. After 100 sec of incubation, 1.51 μL of a 1 mg mL$^{-1}$ solution of *E. coli* nitroreductase in water was added in the quartz fluorescence cell and the solution was mixed as the monitoring proceeded.

Absorbance Monitoring.

A solution of fluorogenic probe was prepared in 1 mL of phosphate buffered saline (PBS) and 150 µL of the resulting solution transferred into a quartz fluorescence cell. A volume of 1.51 µL of a 50 mM solution of NADH was then added to afford a final concentration of 0.5 mM and the resulting solution was incubated at 25° C. After measuring the absorbance spectrum of the probe at to, a volume of 1.51 µL of a 1 mg.mL$^{-1}$ of *E. coli* nitroreductase in water was added in the quartz fluorescence cell and the solution was mixed. The absorption spectrum of the solution was measured between 400 and 700 nm every 2 min.

Fluorescence Microscopy Imaging

Activation of Probes 2a, 2b and 2c in Live A549 Cells.

Fluorescence images were acquired using a Zeiss Axiovert 200M inverted microscope fitted with an AxioCam MRm camera equipped with a 300 W xenon lamp (Sutter, Novato, Calif.), and Texas red and FITC filters (Chroma, Bellows Falls, Vt.). Lung cancer A549 cells (ATCC CCL-185) were grown on glass bottom microwell disks (MatTek Corporation, MA, USA) at a cell density of 10,000 cells/well at 37° C. for 24 hours. When the cell confluence reached ~60-70%, the cells were rinsed three times with phosphate buffered saline (PBS). The cells were treated with 2a, 2b, and 2c at 1, 2.5, 5 and 10 µM concentrations for 1, 2, and 4 hours. Then the cells were stained using 2.5 µg/mL DAPI (Invitrogen) and 100 nM MitoTracker Green FM (Cell Signaling Technology, Inc.) for 40 min. Thereafter, all images were recorded and the target cells counted using a 40× oil objective. To ensure accurate intensity measurements, the exposure time and laser time were kept the same. Pixel intensity was quantified using AxioVision release 4.7 version software, and the mean pixel intensity was generated as gray level. Data are reported as the mean of three independent experiments.

Activation of Prodrugs 4a and 4b in Live A549 Cells.

Fluorescence microscopy images were acquired using a Zeiss Axiovert 200M inverted microscope fitted with an AxioCam MRm camera equipped with a 300 W xenon lamp (Sutter, Novato, Calif., USA), and DAPI (blue channel) and Texas red (red channel) filters (Chroma, Bellows Falls, Vt., USA). A549 cells were grown on glass bottom microwell disks (MatTek Corporation, MA, USA) at a cell density of 10000 cells/well at 37° C. for 24 hours. When the cell confluence reached ~60-70%, the cells were rinsed three times with phosphate buffered saline (PBS). The cells were then treated with AMA, 4a and 4b at 25 µM concentration for 4 hours. The cells were then stained using 100 nM MitoTracker Green FM (Cell Signaling Technology, Danvers, Mass., USA) for 40 minutes. Thereafter, all images were recorded and counted using a 40× oil objective. To ensure accurate intensity measurements, the exposure time and laser time were kept the same. Data are reported as the mean of three independent experiments.

Biological Activity of AMA and Prodrugs 4a and 4b

MTT Toxicity Assays.

Exponentially growing A459 cells were harvested and plated in 96-well plates at a concentration of 2×10$^4$ cells/well. After incubation at 37° C. for 24 h, the cells were treated with compounds AMA, 4a and 4b at final concentrations of 1, 5 and 10 µM for an additional 24 hours. Then 20 µL of MTT (5 mg/mL) was added to each well and the plates were incubated at 37° C. for 4 h. The supernatants were discarded, and 100 µL of DMSO was added to each well. The absorbance was recorded at 490 nm after 15 min. Cell viability was determined by the following formula:

cell viability (%)=100−(OD$_{negative\ control}$−OD$_{treatment}$)×100%/(OD$_{negative\ control}$−OD$_{background}$).

Data are reported as the mean of three independent experiments, each run was carried out quintuplicate.

NADH Oxidase Activity.

The effect of compounds AMA, 4a and 4b on NADH oxidase activity were evaluated using bovine heart mitochondria. The bovine heart mitochondria and bovine heart submitochondrial particles (SMPs) were prepared as described.[2] The SMPs were diluted to 0.5 mg/mL, and the test compounds were assayed at 25° C. and monitored spectrophotometrically using a Beckman Coulter DU-530 spectrometer (340 nm, c 6.22 mM$^{-1}$ cm$^{-1}$). NADH oxidase activity was determined in 1 mL of 50 mM Hepes buffer containing 5 mM MgCl$_2$, pH 7.5. The final mitochondrial protein concentration was 30 µg/mL. The initial rates of NADH oxidation were calculated from the linear portion of the traces. Data are reported as the mean of three independent experiments each run in triplicate.

REFERENCES and FOOTNOTES (1) (a) Wallace, D. C. *Nat. Rev. Cancer* 2012, 12, 685. (b) Sullivan, L. B.; Chandel, N. S. *Cancer Metab.* 2014, 2, 1712, 685. (c) Weinberg, S. E.; Chandel, N. S. *Nat. Chem. Biol.* 2015, 11, 9.

(2) (a) Lessene, G.; Czabotar, P. E.; Colman, P. M. *Nat. Rev. Drug Discov.* 2008, 7, 989. (b) Kang, M. H.; Reynolds, C. P. *Clin. Cancer Res.* 2009, 15, 1126. (c) Yeh, C.-T.; Su, C.-L.; Huang, C.-Y. F.; Lin, J. K.-Y.; Lee, W.-H.; Chang, P. M.-H.; Kuo, Y.-L.; Liu, Y.-W.; Wang, L.-S.; Wu, C.-H.; Shieh, Y.-S.; Jan, Y.-H.; Chuang, Y.-J.; Hsiao, M.; Wu, A. T. H. *Evid.-Based Comp. Alt. Med.* 2013, Art. ID 910451.

(3) (a) Rin Jean, S.; Tulumello, D. V.; Wisnovsky, S. P.; Lei, E. K.; Pereira, M. P.; Kelley, S. O. *ACS Chem. Biol.* 2014, 9, 323. (b) Ma, J.; Lim, C.; Sacher, J. R.; Van Houten, B.; Qian, W.; Wipf, P. *Bioorg. Med. Chem. Lett.* 2015, 25, 4828.

(4) Xu, Z.; Xu, L. *Chem. Commun.* 2016, 52, 1094.

(5) Kratz, F.; Mueller, I. A.; Ryppa, C.; Warnecke, A. *Chem. Med. Chem.* 2008, 3, 20.

(6) Clearly, it would also be possible to employ this strategy in conjunction with an organelle targeting strategy.

(7) Gray, M. W.; Burger, G.; Lang, B. F. *Science* 1999, 283, 1476. (b) Herrmann, J. M. *Trends Microbiol.* 2003, 11, 74.

(8) Symons, Z. C.; Bruce, N. C. *Nat. Prod. Rep.* 2006, 23, 845.

(9) Williams, E. M.; Little, R. F.; Mowday, A. M.; Rich, M. H.; Chan-Hyams, J. V. E.; Copp, J. N.; Smaill, J. B.; Patterson, A. V.; Ackerley, D. F. *Biochem. J.* 2015, 471, 131.

(10) Li, Y.; Sun, Y.; Li, J.; Su, Q.; Yuan, W.; Dai, Y.; Han, C.; Wang, Q.; Feng, W.; Li, F. I *Am. Chem. Soc.* 2015, 137, 6407.

(11) (a) Moreno, S. N. J.; Mason, R. P.; Docampo, R. *J. Biol. Chem.* 1984, 259, 6298. (b) Smyth, G. E.; Orsi, B. A. *Biochem. J.* 1989, 257, 859.

(12) Elmes, R. B. P. *Chem. Commun.* 2016.

Figure 16:
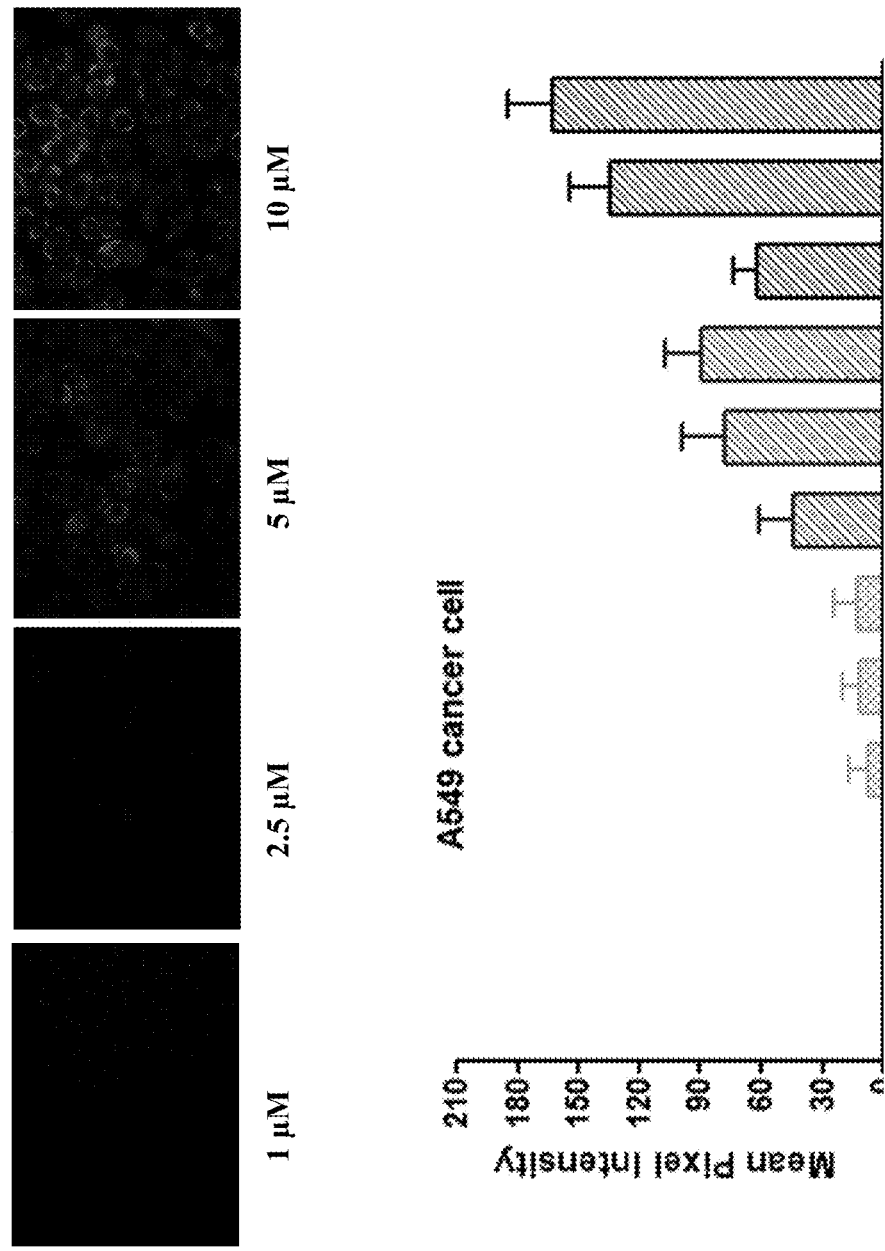
FIG. 16 demonstrates activation of 2c by mitochondrial nitroreductase in live A459 cells. (top) Visualization with red channel at different concentrations after 4 h incubation using an exposure time of 4.8 sec. (bottom) Quantitative analysis of the red fluorescent signal in A549 cell mitochondria produced from 2c at different times and concentrations with an exposure time of 4.8 sec.

(13) (a) Dickinson, B. C.; Chang, C. J. *J. Am Chem. Soc.* 2008, 130, 9638. (b) Dodani, S. C.; Leary, S. C.; Cobine, P. A.; Winge, D. R.; Chang, C. J. I *Am. Chem. Soc.* 2011, 133, 8606. (c) Kong, X.; Su, F.; Zhang, L.; Yaron, J.; Lee, F.; Shi, Z.; Tian, Y.; Meldrum, D. R. *Angew. Chem. Int. Ed.* 2015, 54, 12053. (d) Yuan, L.; Wang, L.; Agrawalla,

(14) B. K.; Park, S.-J.; Zhu, H.; Sivaraman, B.; Peng, J.; Xu, Q.-H.; Chang, Y.-T. *J. Am Chem. Soc.* 2015, 137, 5930.
(14) A similar strategy has been used to unmask a methylene blue derivative in *E. coli*. See Bae, J.; McNamara, L. E.; Nael, M. A.; Mandi, F.; Doerksen, R. J.; Bidwell, G. L., III; Hammer, N. I.; Jo, S. *Chem Commun.* 2015, 51, 12787.
(15) (a) Karton-Lifshin, N.; Segal, E.; Omer, L.; Portnoy, M.; Satchi-Fainaro, R.; Shabat, D. *J. Am. Chem. Soc.* 2011, 133, 10960. (b) Redy-Keisar, O.; Kisin-Finfer, E.; Ferber, S.; Satchi-Fainaro, R.; Shabat, D. *Nat. Protoc.* 2014, 9, 27.
(16) The use of a greater (5 μg mL$^{-1}$) concentration of NTR also failed to produce any detectable activation of the probe.
(17) Danson, S.; Ward, T. H.; Butler, J.; Ranson, M. *Cancer Treat. Rev.* 2004, 30, 437.
(18) As a control, probes 2a and 2b have also been tested, and not provide a good signal (FIGS. 14 and 15). For 2b this is understandable as no elimination process is possible, as confirmed during the in vitro tests. In the case of 2a, we assume that the low kinetics of the reduction (c.f. FIG. 6b) is probably the cause of the absence of a strong signal. The appearance of a signal from 2c was also concentration dependent (FIG. 16).
(19) Chevalier, A.; Zhang, Y.; Khdour, 0. M.; Hecht, S. M. 2016, *Org. Lett.* 2016, 18.
(20) Tzung, S.-P.; Kim, K. M.; Basanez, G.; Giedt, C. D.; Simon, J.; Zimmerberg, J.; Zhang, K. Y. J.; Hockenbery, D. M. *Nat. Cell Biol.* 2001, 3, 183.
(21) In comparison, A549 cells treated with AMA resulted in a distribution of AMA which did not fully colocalize with mitochondria (FIG. 17).
(22) Huang, L-S.; Cobessi, D.; Tung, E. Y.; Berry, E. A.; *J. Mol. Biol.* 2005, 351, 573.

We claim:

1. A compound having the formula:

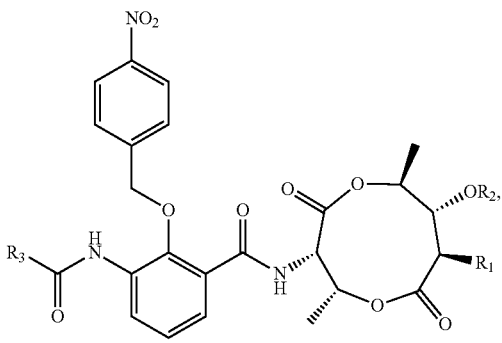

wherein $R_1$ and $R_3$ are independently H, aryl or alkyl, and $R_2$ is an acyl group.

2. A pharmaceutical composition comprising a profluorescent compound having the formula, or an ortho-substituted analogue thereof:

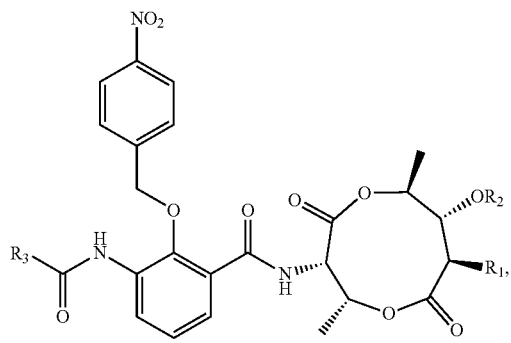

wherein $R_1$ and $R_3$ are independently H, aryl or alkyl groups, and $R_2$ is an acyl group or a group chemically modifiable to an acyl group; and a pharmaceutically acceptable carrier.

3. A method for imaging mitrochondria, the method comprising:
contacting the compound as described in claim 2 to a target cell;
detecting a nitrobenzyl fluorescence signal in one or more mitochondria of the cell.

4. A method for selective delivery of a therapeutic agent to a mitochondrion of target cell, the method comprising contacting a target cell to the compound as described in claim 2 operably linked to a therapeutic agent, whereby the therapeutic agent is selectively activated upon entry to a mitochondrion of target cell.

5. A pharmaceutical composition comprising a compound as described in claim 1 and a pharmaceutically acceptable carrier.

6. A method for imaging mitrochondria, the method comprising:
contacting the compound as described in claim 1 to a target cell;
detecting a nitrobenzyl fluorescence signal in one or more mitochondria of the cell.

7. A method for selective delivery of a therapeutic agent to a mitochondrion of target cell, the method comprising contacting a target cell to the compound as described in claim 1 operably linked to a therapeutic agent, whereby the therapeutic agent is selectively activated upon entry to a mitochondrion of target cell.

* * * * *